US011471308B2

(12) United States Patent
Kum

(10) Patent No.: US 11,471,308 B2
(45) Date of Patent: Oct. 18, 2022

(54) EXTRAVASCULAR BYPASS SYSTEMS AND METHODS

(71) Applicant: Wei Cheong Steven Kum, Singapore (SG)

(72) Inventor: Wei Cheong Steven Kum, Singapore (SG)

(*) Notice: Subject to any disclaimer, the term of this patent is extended or adjusted under 35 U.S.C. 154(b) by 108 days.

(21) Appl. No.: 16/877,262

(22) Filed: May 18, 2020

(65) Prior Publication Data
US 2020/0368047 A1 Nov. 26, 2020

Related U.S. Application Data

(60) Provisional application No. 62/850,515, filed on May 20, 2019.

(51) Int. Cl.
*A61F 2/82* (2013.01)
*A61B 17/12* (2006.01)
*A61F 2/958* (2013.01)

(52) U.S. Cl.
CPC .......... *A61F 2/82* (2013.01); *A61B 17/12118* (2013.01); *A61F 2/958* (2013.01); *A61F 2002/823* (2013.01)

(58) Field of Classification Search
CPC .................. A61F 2/82; A61F 2002/826; A61F 2002/828; A61F 2/848; A61F 2/958; A61F 2220/0025; A61F 2220/0075; A61F 2230/0052; A61F 2250/0007; A61F 2250/0013; A61F 2250/006; A61F 2250/0062
See application file for complete search history.

(56) References Cited

U.S. PATENT DOCUMENTS

| 2,935,068 | A | * | 5/1960 | Donaldson | A61M 60/148 604/175 |
| 4,230,119 | A | * | 10/1980 | Blum | A61B 17/12045 606/194 |
| 5,211,683 | A | | 5/1993 | Maginot | |

(Continued)

FOREIGN PATENT DOCUMENTS

| WO | WO-9514442 A1 | 6/1995 |
| WO | WO-2018/215469 A1 | 11/2018 |

OTHER PUBLICATIONS

International Search Report & Written Opinion dated Aug. 7, 2020 in Int'l PCT Patent Appl. Serial No. PCT/IB2020/054708 (0210).

(Continued)

*Primary Examiner* — Paul B Prebilic
(74) *Attorney, Agent, or Firm* — Eversheds Sutherland (US) LLP; Christopher C. Bolten; Albert K. Heng

(57) ABSTRACT

Systems and methods are provided for extravascularly bypassing an occlusion within a patient's blood vessel. An upstream bypass stent may be implanted at an implant site upstream of the occlusion and a downstream bypass stent may be implanted at an implant site downstream of the occlusion, wherein an outlet of the upstream stent and an inlet of the downstream stent are coupled extravascularly to permit blood to extravascularly bypass the occlusion. The upstream stent further may include an additional outlet that directs blood to flow through the occluded blood vessel. A kit including a percutaneous tumescence tunneler for implanting the extravascular bypass system is also provided.

17 Claims, 20 Drawing Sheets

(56) References Cited

U.S. PATENT DOCUMENTS

| | | | | |
|---|---|---|---|---|
| 5,443,497 | A | * | 8/1995 | Venbrux .................. A61F 2/06 604/8 |
| 5,755,772 | A | * | 5/1998 | Evans ...................... A61F 2/07 128/898 |
| 5,961,548 | A | | 10/1999 | Shmulewitz |
| 6,190,353 | B1 | | 2/2001 | Makower et al. |
| 6,287,335 | B1 | | 9/2001 | Drasler et al. |
| 6,936,060 | B2 | | 8/2005 | Hogendijk et al. |
| 7,100,617 | B1 | * | 9/2006 | Maginot ................ A61B 17/11 128/898 |
| 7,374,567 | B2 | | 5/2008 | Heuser |
| 8,062,321 | B2 | | 11/2011 | Heuser et al. |
| 8,545,418 | B2 | | 10/2013 | Heuser |
| 8,808,261 | B2 | | 8/2014 | Berent et al. |
| 8,864,810 | B2 | | 10/2014 | Clamote et al. |
| 8,945,202 | B2 | | 2/2015 | Mayberry et al. |
| 8,974,518 | B2 | | 3/2015 | Bruszewski et al. |
| 9,301,830 | B2 | | 4/2016 | Heuser et al. |
| 10,182,902 | B2 | | 1/2019 | Heuser et al. |
| 10,278,851 | B2 | | 5/2019 | Reis et al. |
| 2014/0148751 | A1 | | 5/2014 | Kassab et al. |
| 2018/0271638 | A1 | | 9/2018 | Hall et al. |
| 2019/0022368 | A1 | | 1/2019 | Hall et al. |

OTHER PUBLICATIONS

Glickman, M.D., Marc, Eastern Virginia Medical School, HeRo Device: Indications and Outcomes, http://www.cryolife.com/wp-content/uploads/stories/assets/docs/glickman_veith_abstract.pdf, retrieved Apr. 2019.

Merit Medical, Peripheral Intervention, HeRo Graft Product Brochure, https://www.merit.com/wp-content/uploads/2016/02/401512001-A_HeRO_Product-Brochure_US..160209.1500.pdf, retrieved Apr. 2019.

Sarradon, Pierre, Totally Percutaneous Bypass, The best of two worlds, LINC, Jan. 24, 2019, available at https://linc2019.cncptdix.com/media/1330_Pierre_Sarradon_24_01_2019_Room_6_-_Speakers_corner_v2.pdf.

* cited by examiner

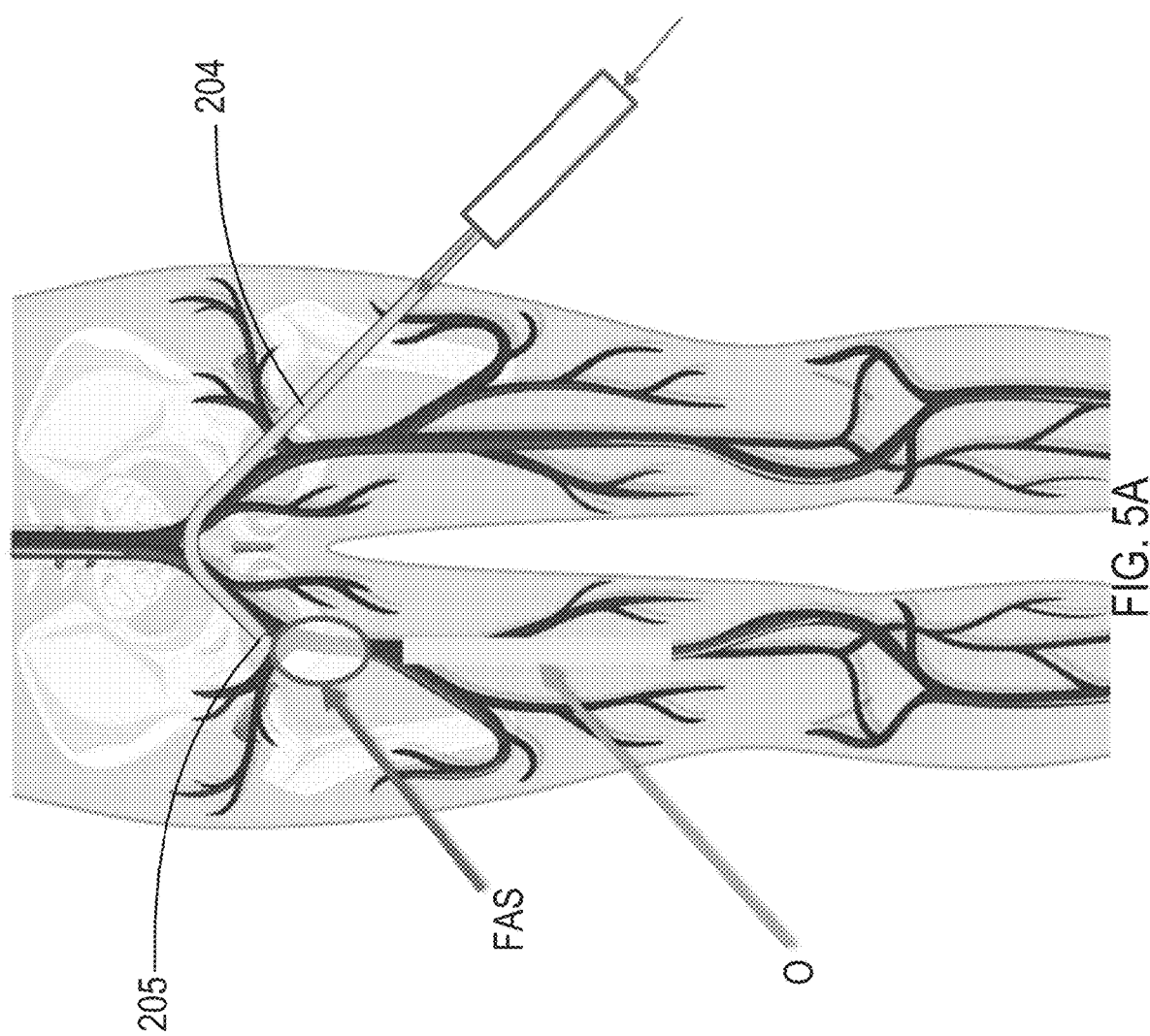

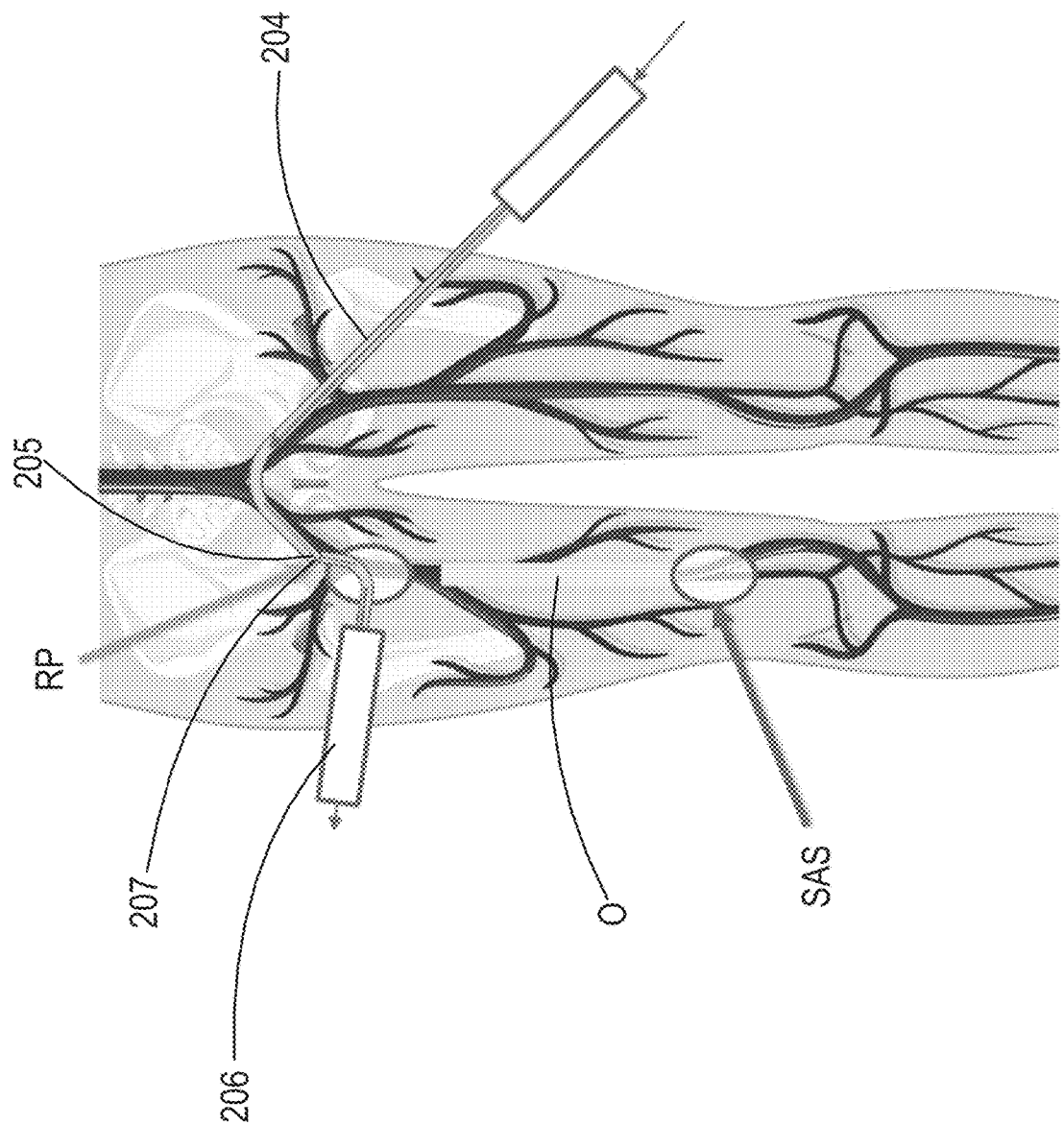

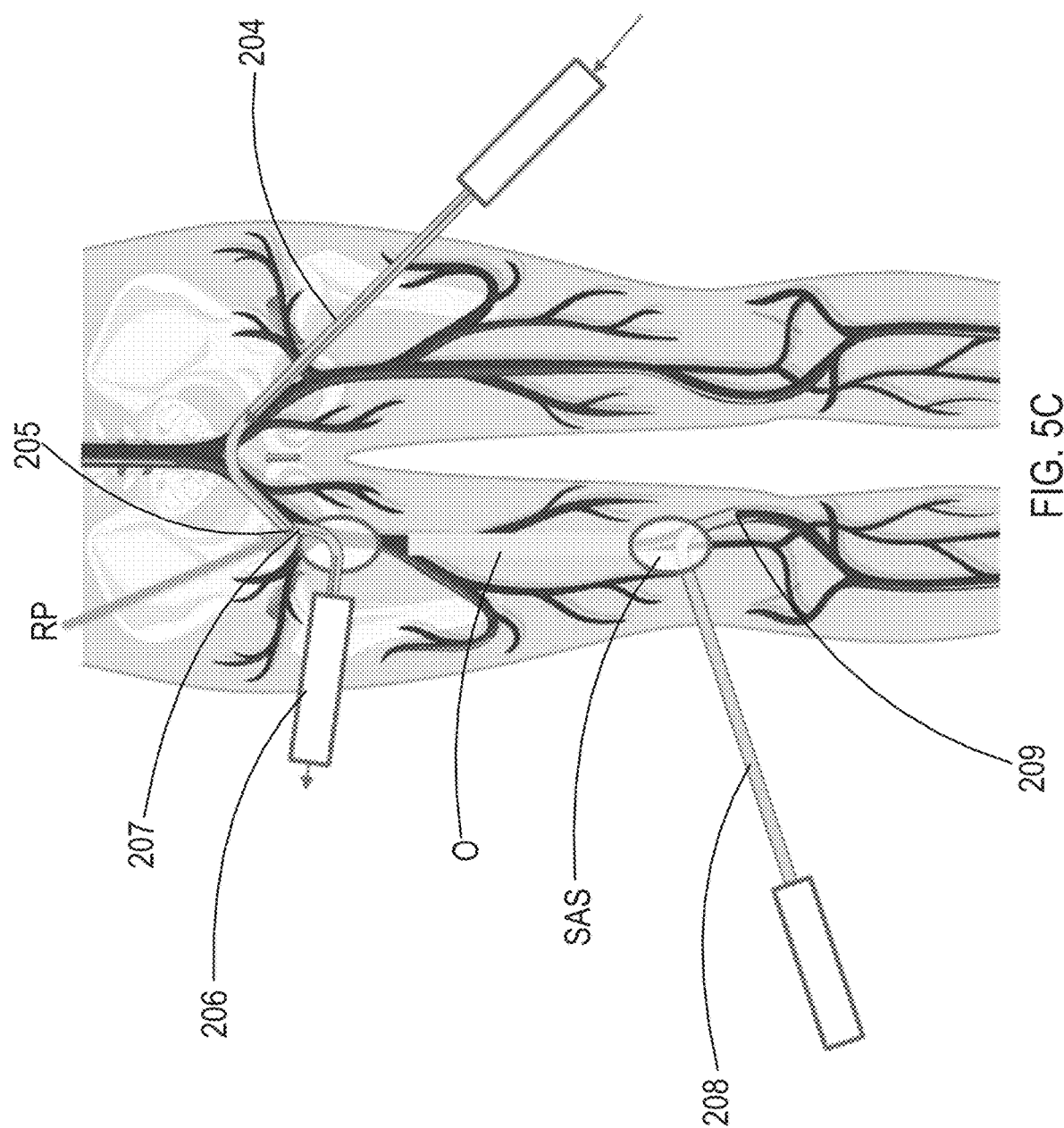

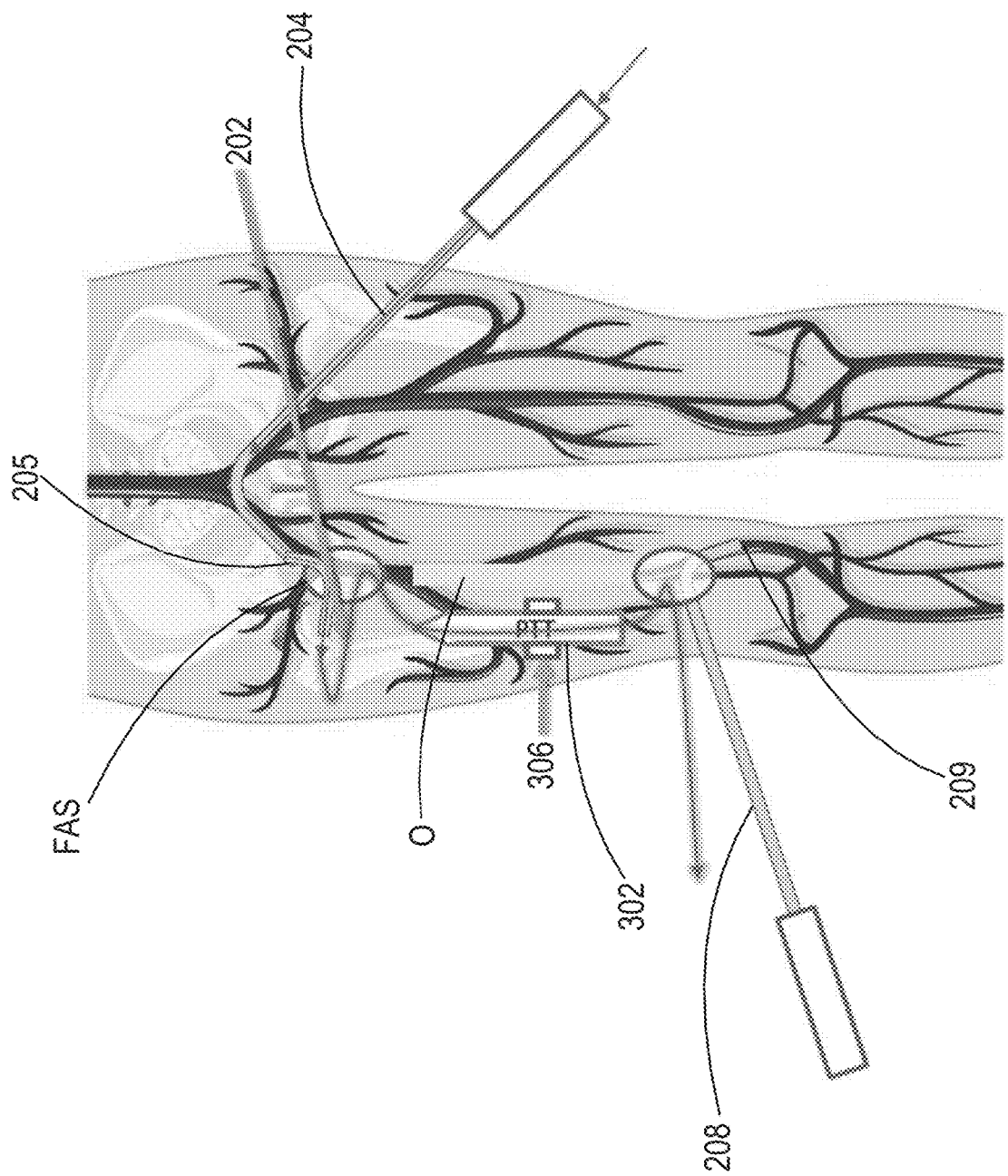

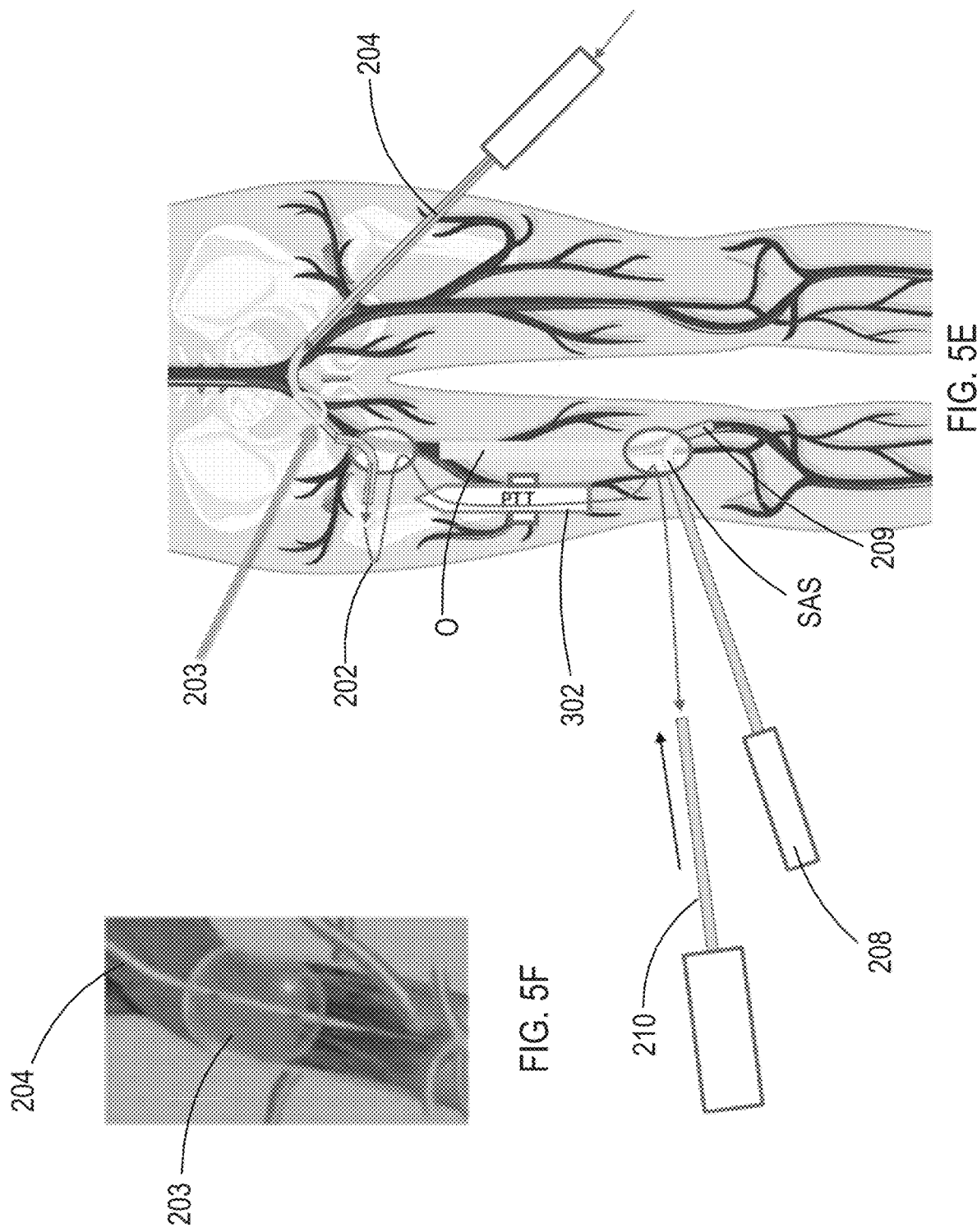

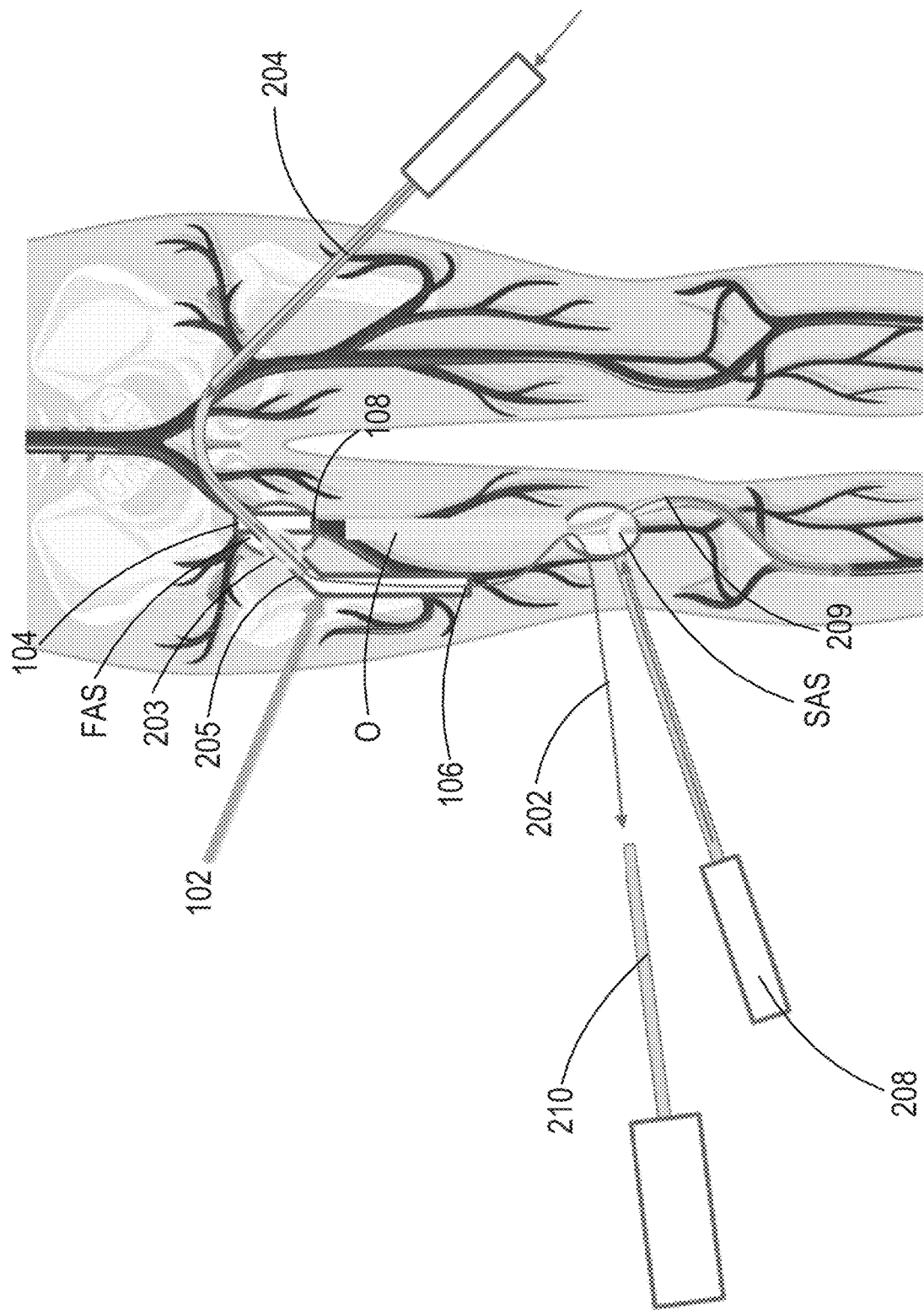

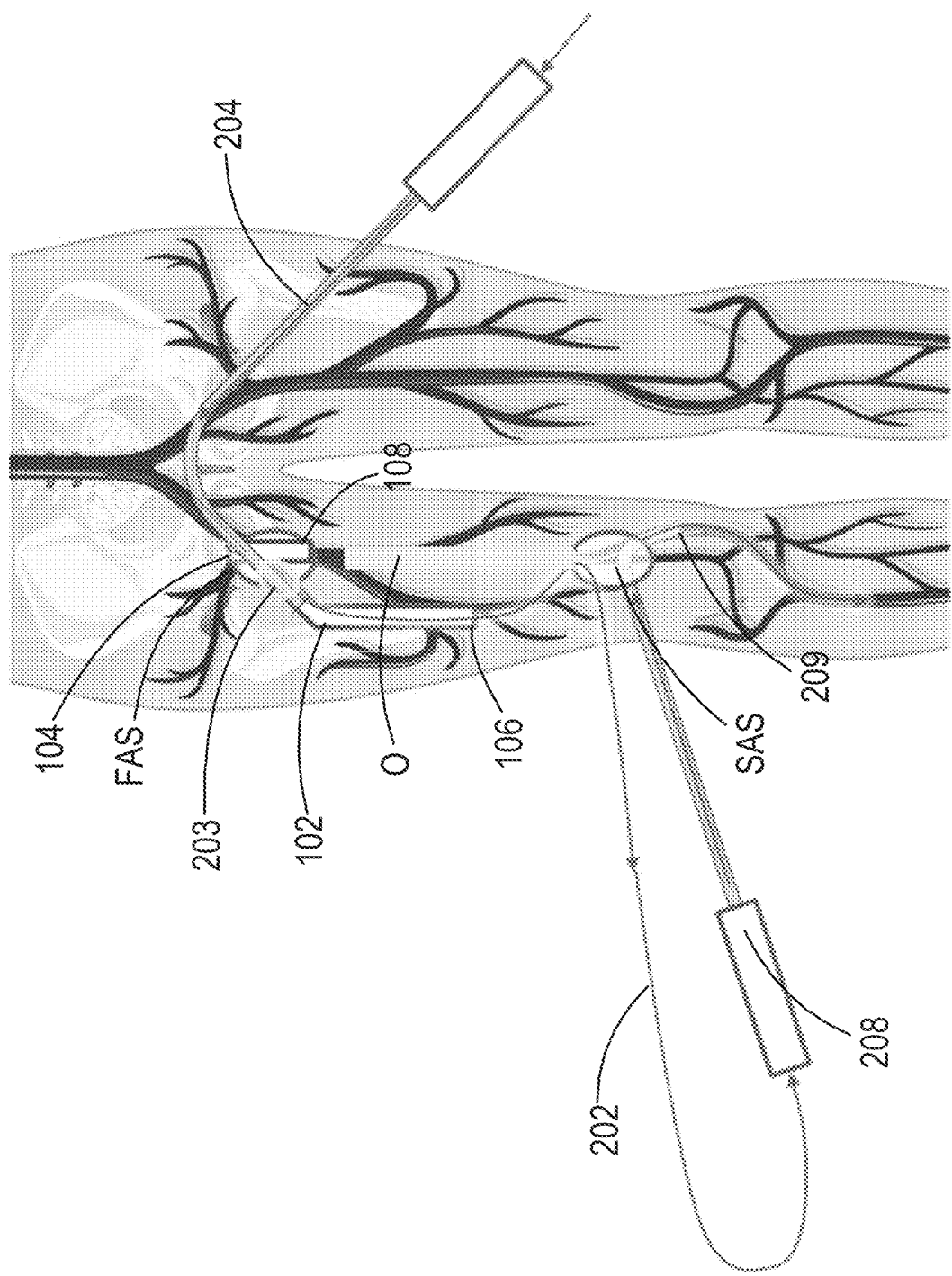

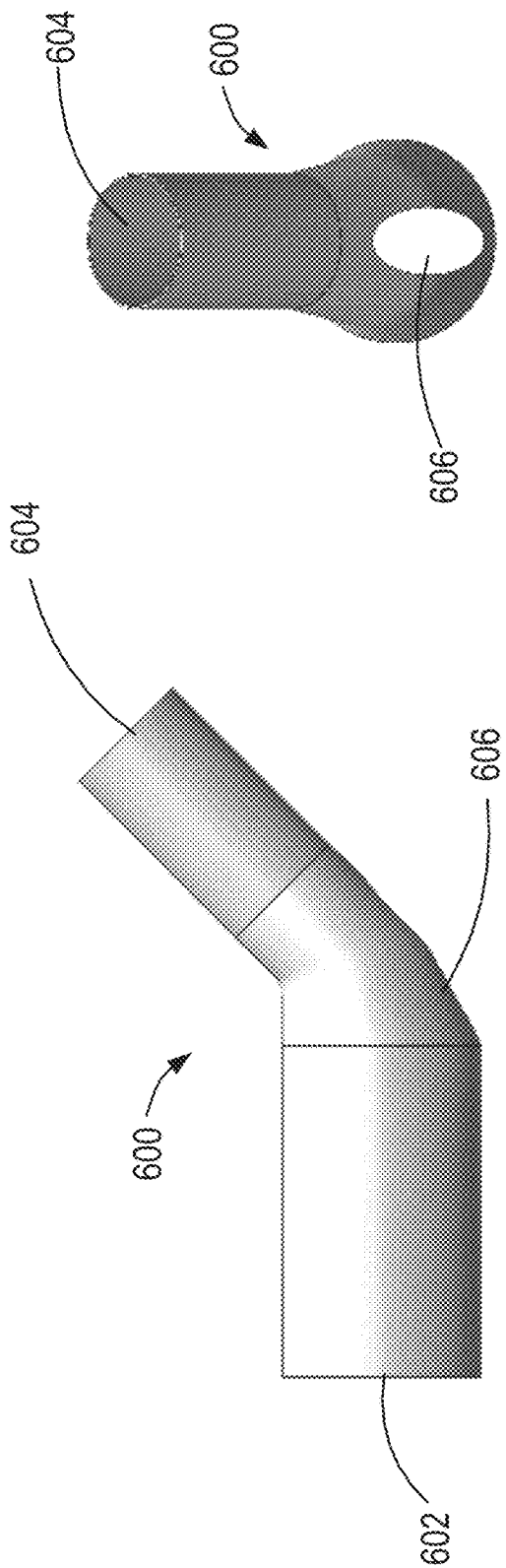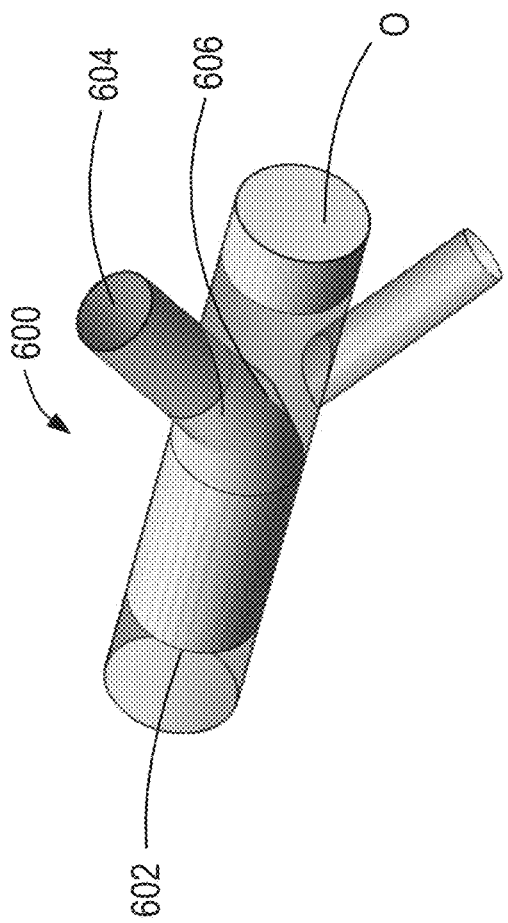
FIG. 6A
FIG. 6B
FIG. 6C

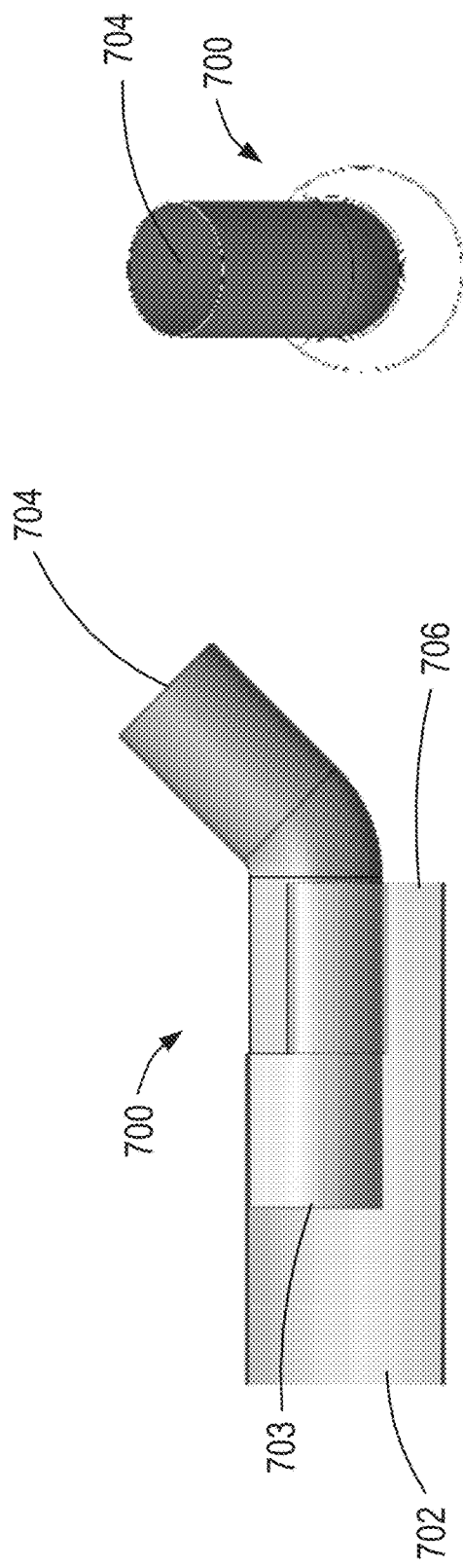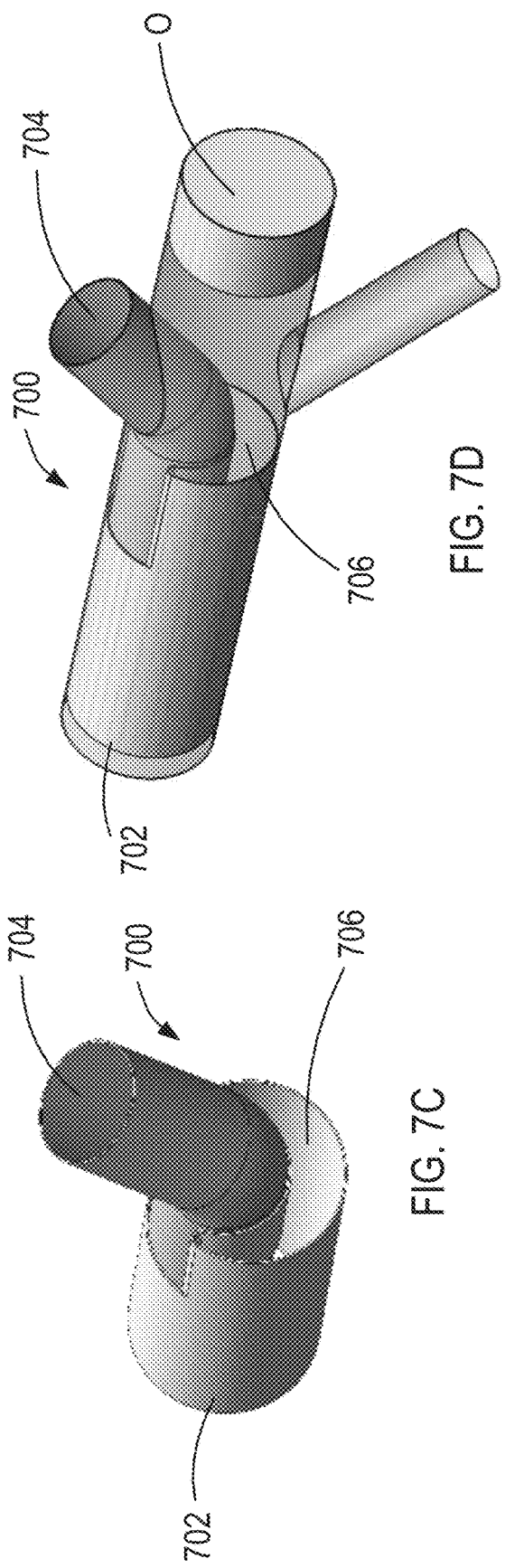
FIG. 7A
FIG. 7B
FIG. 7C
FIG. 7D

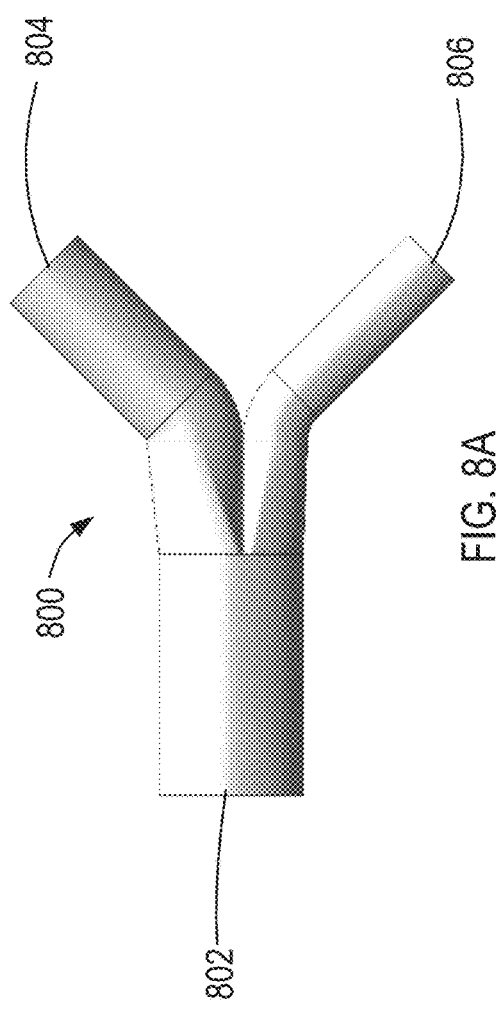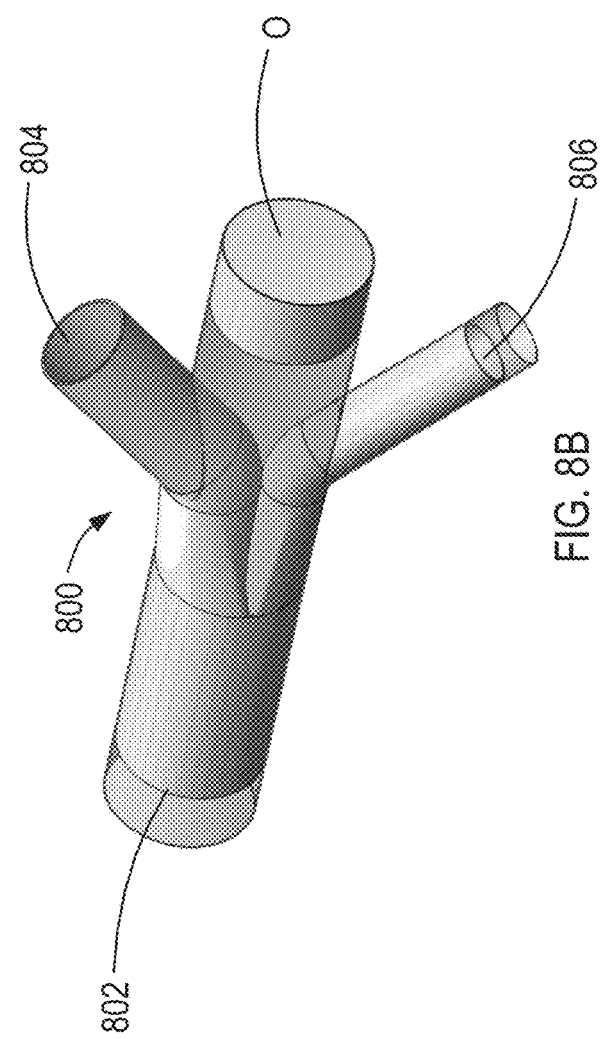

EXTRAVASCULAR BYPASS SYSTEMS AND METHODS

CROSS-REFERENCE TO RELATED APPLICATIONS

This application claims the benefit of priority of U.S. Provisional Patent Application No. 62/850,515, filed May 20, 2019, the entire contents of which are incorporated herein by reference.

FIELD OF THE INVENTION

This application generally relates to systems and methods for minimally invasive extravascular bypass in the peripheral vasculature.

BACKGROUND OF THE INVENTION

Many people suffering from peripheral artery disease suffer from insufficient blood flow to peripheral regions of their body. This may be caused by the narrowing of one or more peripheral arteries, e.g., a superficial femoral artery, to their peripheral extremities, e.g., legs or arms. A common cause of such narrowing is due to the development of occlusions within the blood vessel. Such narrowing of the vessels may reduce blood flow to one or more peripheral regions. Insufficient blood flow to the extremities of the body can lead to critical limb ischemia, gangrene, and/or amputation.

Previous attempts to restore normal blood flow through the vessel includes ablating the occlusion to clear the passageway through the vessel as described in U.S. Pat. No. 8,545,418 to Heuser, or to surgically bypass the occlusion. For example, U.S. Pat. No. 8,062,321 to Heuser describes systems and methods for creating a fistula between two adjacent blood vessels to allow blood to exit the occluded vessel upstream of the occlusion, flow into the adjacent vessel, and back in to the original vessel at a point downstream of the occlusion.

An issue arises in co-locating the openings in the two blood vessels and holding the vessel walls in place to ensure that a channel will be created between the vessels so that blood will flow from one vessel to the other. Another issue involves aiming and maintaining the position of the catheters inside the vessels. In particular, veins often have diameters much larger than arteries, making hitting a smaller artery from a larger vein difficult. Additionally, larger veins often allow a catheter too much freedom of movement inside the vein.

Example publications include: U.S. Pat. Nos. 6,190,353, 6,936,060, 7,374,567, 8,062,321, 8,545,418, 8,808,261, 8,864,810, 9,301,830, 10,182,902, and 10,278,851, U.S. Patent Application Nos. 2014/0148751, 2018/0271638, and 2019/0022368, International PCT Publication No. WO 2018/215469, Sarradon, P. Totally Percutaneous Bypass, The best of two worlds, LINC, Jan. 24, 2019, available at https://linc2019.cncptdlx.com/media/1330_Pierre_Sarradon_24_01_2019_Room_6_-_Speakers_corner_v2.pdf, Merit Medical Peripheral Intervention Hero Graft Product Brochure, retrieved April 2019, available at https://www.merit.com/wp-content/uploads/2016/02/401512001-A_HeRO_Product-Brochure_US . . . 160209.1500.pdf, and Glickman, M. H., et al. HeRo Device: Indications And Outcomes, retrieved April 2019, available at http://www.cryolife.com/wp-content/uploads/stories/assets/docs/glickman_veith_abstract.pdf.

Therefore, it is desirable to provide more effective systems and methods for bypassing an occlusion within a patient's blood vessel.

SUMMARY OF THE INVENTION

The present invention provides systems and methods for extravascularly bypassing an occlusion within a patient's blood vessel, and a kit for implanting the extravascular bypass system. For example, the extravascular bypass system includes an upstream bypass stent having an upstream bypass inlet sized and shaped to be implanted within at least one blood vessel at a first implant site upstream of an occlusion within the at least one blood vessel. The upstream bypass stent further includes a first upstream bypass outlet in fluid communication with the upstream bypass inlet, and sized and shaped to be implanted extravascularly, and a second upstream bypass outlet in fluid communication with the upstream bypass inlet, the second upstream bypass outlet sized and shaped to direct blood flow from the upstream bypass inlet toward the second upstream bypass outlet.

In addition, the extravascular bypass system includes a downstream bypass stent having a first downstream bypass inlet sized and shaped to be implanted extravascularly and to be coupled to the first upstream bypass outlet of the upstream bypass stent such that the first downstream bypass inlet is in fluid communication with the upstream bypass inlet of the upstream bypass stent. The downstream bypass stent further includes a downstream bypass outlet sized and shaped to be implanted within the at least one blood vessel at a second implant site downstream of the occlusion within the at least one blood vessel, the downstream bypass outlet in fluid communication with the upstream bypass inlet of the upstream bypass stent via the first upstream bypass outlet of the upstream bypass stent and the first downstream bypass inlet such that blood flow through the upstream bypass inlet is directed to bypass the occlusion via the first upstream bypass outlet, the first downstream bypass inlet, and the downstream bypass outlet.

In accordance with one aspect of the present invention, the downstream bypass stent further includes a second downstream bypass inlet in fluid communication with the downstream bypass outlet, the second downstream bypass inlet positioned downstream of the occlusion within the at least one blood vessel such that blood flow through the upstream bypass inlet is directed out the downstream bypass outlet via the second upstream bypass outlet and the second downstream bypass inlet. Moreover, the downstream bypass stent further may include a tube having a first end and a second end, the first end coupled to the second downstream bypass inlet, and the second end sized and shaped to be implanted within the vessel at a location downstream of the occlusion within the vessel, the second end having a tube inlet in fluid communication with the second downstream bypass inlet of the downstream bypass stent.

The first upstream bypass outlet of the upstream bypass stent and the first downstream bypass inlet of the downstream bypass stent may be implanted subcutaneously. In accordance with another aspect of the present invention, the second upstream bypass outlet of the upstream bypass stent includes one or more fenestrations. In addition, the upstream bypass stent further may include a tube having a first end and a second end, the first end coupled to the second upstream bypass outlet, and the second end sized and shaped to be implanted within the vessel at a location upstream of the occlusion within the vessel, the second end having a tube outlet in fluid communication with the second upstream bypass outlet of the upstream bypass stent.

In accordance with the principles of the present invention, a kit for implanting the extravascular bypass system may include a first sheath having a distal end sized and shaped to be positioned within the vessel adjacent the first implant site via a contralateral access point, the first sheath having a length extending at least from the contralateral access point to the first implant site. The distal end of the first sheath may include an inflatable balloon transitionable between a deflated delivery state and an inflated state having a size and shape to stop blood flow through the vessel.

Further, the kit further includes a second sheath, e.g., a peel-away sheath, having a distal end sized and shaped to be positioned adjacent the distal end of the first sheath via a first access point upstream of the occlusion within the vessel, the second sheath having a length extending at least from the first access point to the distal end of the second sheath. Additionally, the kit further includes a third sheath, e.g., a peel-away sheath, having a distal end sized and shaped to be positioned within the vessel adjacent the second implant site via a second access point downstream of the occlusion within the vessel, the third sheath having a length extending at least from the second access point to the distal end of the third sheath.

In addition, the kit further includes a percutaneous tumescence tunneler having a length extending from the first access site to the second access site. The kit also may include a first delivery sheath having a lumen extending therethrough sized and shaped to deliver the upstream bypass stent in a collapsed delivery state to the first implant site, and a second delivery sheath having a lumen extending therethrough sized and shaped to deliver the downstream bypass stent in a collapsed delivery state to the second implant site, such that the first upstream bypass outlet of the upstream bypass stent and the first downstream bypass inlet of the downstream bypass stent overlap in a deployed state. The kit further may include a guidewire having a length extending at least from the contralateral access point to the first access point and the second access point.

In accordance with another aspect of the present invention, a method for extravascularly bypassing an occlusion within a vessel of a patient. The method includes implanting the upstream bypass stent at a first implant site upstream of the occlusion within the vessel, the upstream bypass stent having an upstream bypass inlet, a first upstream bypass outlet extending extravascularly from the first implant site, the first upstream bypass outlet in fluid communication with the upstream bypass inlet, and a second upstream bypass outlet upstream of the occlusion in fluid communication with the upstream bypass inlet. The method further includes implanting the downstream bypass stent at a second implant site downstream of the occlusion within the vessel, the downstream bypass stent having a first downstream bypass inlet extending extravascularly from the second implant site, and a downstream bypass outlet in fluid communication with first and second downstream bypass inlets.

The method also includes coupling the first upstream bypass outlet of the upstream bypass stent with the first downstream bypass inlet of the downstream bypass stent, and permitting blood to flow through the upstream bypass inlet to bypass the occlusion via the first upstream bypass outlet, the first downstream bypass inlet, and the downstream bypass outlet, and to flow through the upstream bypass inlet to the downstream bypass outlet via the second upstream bypass outlet. When the downstream bypass stent includes a second downstream bypass inlet in fluid communication with the downstream bypass outlet downstream of the occlusion, blood is permitted to flow through the upstream bypass inlet to the downstream bypass outlet via the second upstream bypass outlet and the second downstream bypass inlet.

For example, implanting the upstream bypass stent at the first implant site may include introducing the distal end of the first sheath through the contralateral access point to the position adjacent the first implant site; introducing the distal end of the second sheath through the first access point upstream of the occlusion to rendezvous with the distal end of the first sheath; introducing the distal end of the third sheath through the second access point downstream of the occlusion; routing the guidewire through the first sheath and the second sheath; percutaneously inserting the tunneler between the first and second access points; routing the guidewire through the tunneler from the first access point to the second access point; introducing the first delivery sheath over the guidewire from the second access point to the first access point, the first delivery sheath having the upstream bypass stent disposed therein in the collapsed delivery state; and implanting the upstream bypass stent at the first implant site using the first delivery sheath.

Moreover, implanting the downstream bypass stent at the second implant site may include introducing the second delivery sheath over the guidewire from the contralateral access point to the second implant site, the second delivery sheath having the downstream bypass stent disposed therein in the collapsed delivery state; and implanting the downstream bypass stent at the second implant site using the second delivery sheath.

BRIEF DESCRIPTION OF THE DRAWINGS

FIGS. 5A-5L illustrate steps taken during the method of FIG. 4, according to some embodiments of the present invention.

FIGS. 6A-6C illustrate an alternative exemplary extravascular bypass stent constructed in accordance with the principles of the present invention.

FIGS. 7A-7D illustrate another alternative exemplary extravascular bypass stent constructed in accordance with the principles of the present invention.

FIGS. 8A and 8B illustrate yet another alternative exemplary extravascular bypass stent constructed in accordance with the principles of the present invention.

DETAILED DESCRIPTION OF THE INVENTION

In view of the foregoing, it would be desirable to provide systems and methods for extravascularly bypassing an occlusion within a patient's blood vessel. For example, the extravascular bypass system may direct blood flow within blood vessel out of the vessel, through an extravascular stent, and back to the blood vessel at a location downstream of the occlusion, thereby bypassing the occlusion within the blood vessel. Moreover, by positioning the bypass stent extravascularly, e.g., not within another blood vessel, the extravascular bypass system will limit disturbances of blood flow through the patient's vascular.

Figure 1:
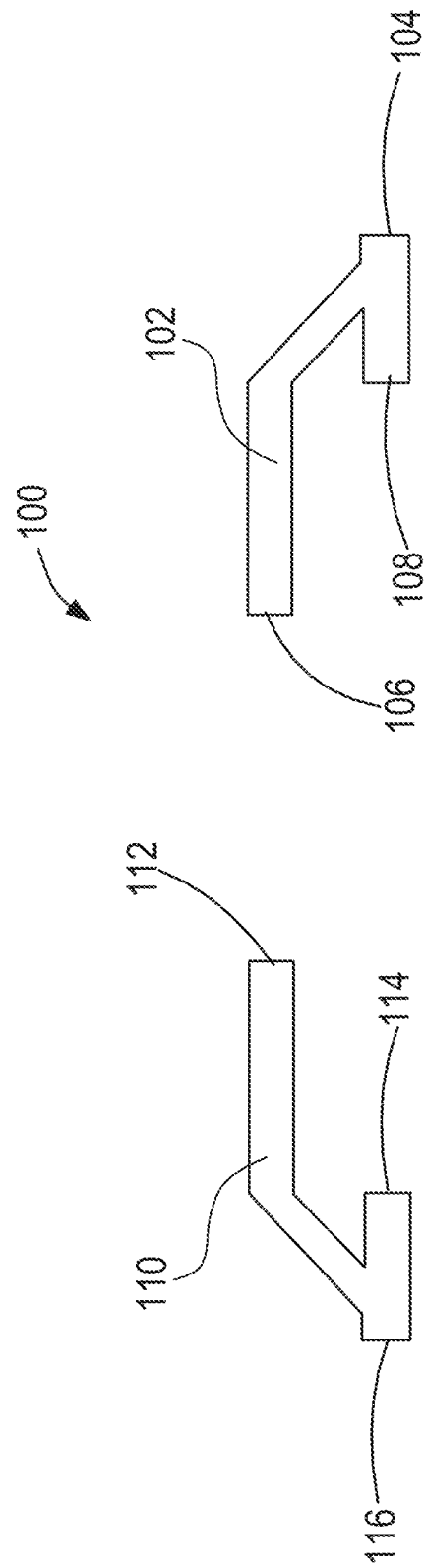
FIG. 1 is an exemplary extravascular bypass system constructed in accordance with the principles of the present invention.

Referring now to FIG. 1, exemplary extravascular bypass system 100 is provided. System 100 includes upstream bypass stent 102 and downstream bypass stent 110. Stent 102 has upstream inlet 104, first upstream bypass outlet 106, and second upstream outlet 108, such that inlet 104, outlet 106 and outlet 108 are all in fluid communication with each other via a lumen extending therebetween. Upstream inlet 104 is sized and shaped to be positioned within a patient's blood vessel, e.g., the external iliac artery, upstream of the occlusion within, e.g., the superficial femoral artery. For example, inlet 104 may have an outer diameter essentially equal to the inner diameter of the blood vessel such that all blood flow through the blood vessel is directed into stent 102.

First upstream outlet 106 may be positioned at the end of a flexible tube sized and shaped to extend from within the patient's blood vessel extravascularly into tissue surrounding the patient's vasculature. For example, outlet 106 may be positioned subcutaneously. In addition, outlet 106 may be threaded and/or have other means for coupling with first downstream inlet 112 as described in more detail below. Accordingly, stent 102 may direct blood flow extravascularly from inlet 104 to outlet 106, to thereby bypass the occlusion within the patient's blood vessel. Thus, the flexible tube having outlet 106 disposed thereon may have a length sufficient to bypass the occlusion.

Stent 102 further includes second upstream outlet 108. Outlet 108 may be positioned at the end of a tube, and sized and shaped to be positioned within the patient's blood vessel downstream of inlet 104, but upstream of the occlusion within the vessel. Accordingly, outlet 108 permits at least some blood entering inlet 104 to exit via outlet 108, e.g., within the blood vessel toward the occlusion. This structure permits the occluded vessel to continue to receive blood flow therethrough while system 100 is implanted, thereby providing, e.g., oxygen to the occluded blood vessel and preventing further damage to the occluded blood vessel. Thus, as blood flow enters inlet 104, it is permitted to bypass the occlusion via outlet 106, as well as continue to flow through the occluded blood vessel via outlet 108.

Downstream bypass stent 110 has first downstream inlet 112, downstream bypass outlet 116, and optional second downstream inlet 114, such that inlet 112, inlet 114, and outlet 116 are all in fluid communication with each other via a lumen extending therebetween.

First downstream inlet 112 may be positioned at the end of a flexible tube sized and shaped to extend from within the patient's blood vessel extravascularly into tissue surrounding the patient's vasculature. For example, inlet 112 may be positioned subcutaneously. In addition, inlet 112 may be threaded and/or have other means for coupling with first upstream outlet 106. For example, the portions of the extravascular tubes having outlet 106 and inlet 112 may have grooves or ridges or any other surface permitting friction-fit coupling therebetween. Thus, either outlet 106 will having an outer diameter slightly less than the inner diameter of inlet 112, or inlet 112 will have an out diameter that is slightly less than the inner diameter of outlet 106. As will be understood by a person having ordinary skill in art, other known coupling means may be utilized including, e.g., adhesives, locking mechanisms, etc. Moreover, for added security, Accordingly, stents 102 and 110 may direct blood flow extravascularly from inlet 104 to outlet 116 via outlet 106 and inlet 112, to thereby bypass the occlusion within the patient's blood vessel. Thus, the flexible tubes having outlet 106 and inlet 106 disposed thereon collectively may have a length sufficient to bypass the occlusion.

Downstream outlet 116 is sized and shaped to be positioned within a patient's blood vessel downstream of the occlusion. For example, outlet 116 may be position within the same vessel downstream of the occlusion, or in a vessel branching off from the occluded vessel, depending on the patient's needs and vasculature. Moreover, outlet 116 may have an outer diameter essentially equal to or less than the inner diameter of the blood vessel such that all blood flow redirected via inlet 104 exits system 100 via outlet 116.

Stent 110 may include second downstream inlet 114. Inlet 114 may be positioned at the end of a tube, and sized and shaped to be positioned within the patient's blood vessel downstream of the occlusion within the vessel, but upstream of outlet 11. Inlet 116 may have an outer diameter essentially equal to or less than the inner diameter of the blood vessel such that all blood flow through the occluded vessel via outlet 108 may be directed into stent 110 and exit outlet 116 via inlet 114. Accordingly, inlet 116 permits at least some blood flowing through the occluded vessel to exit via outlet 116. Thus, as blood flow enters inlet 104, it is permitted to bypass the occlusion via outlet 106, inlet 112, and outlet 116, as well as continue to flow through the occluded blood vessel via outlet 108, inlet 114, and outlet 116.

Figure 2:
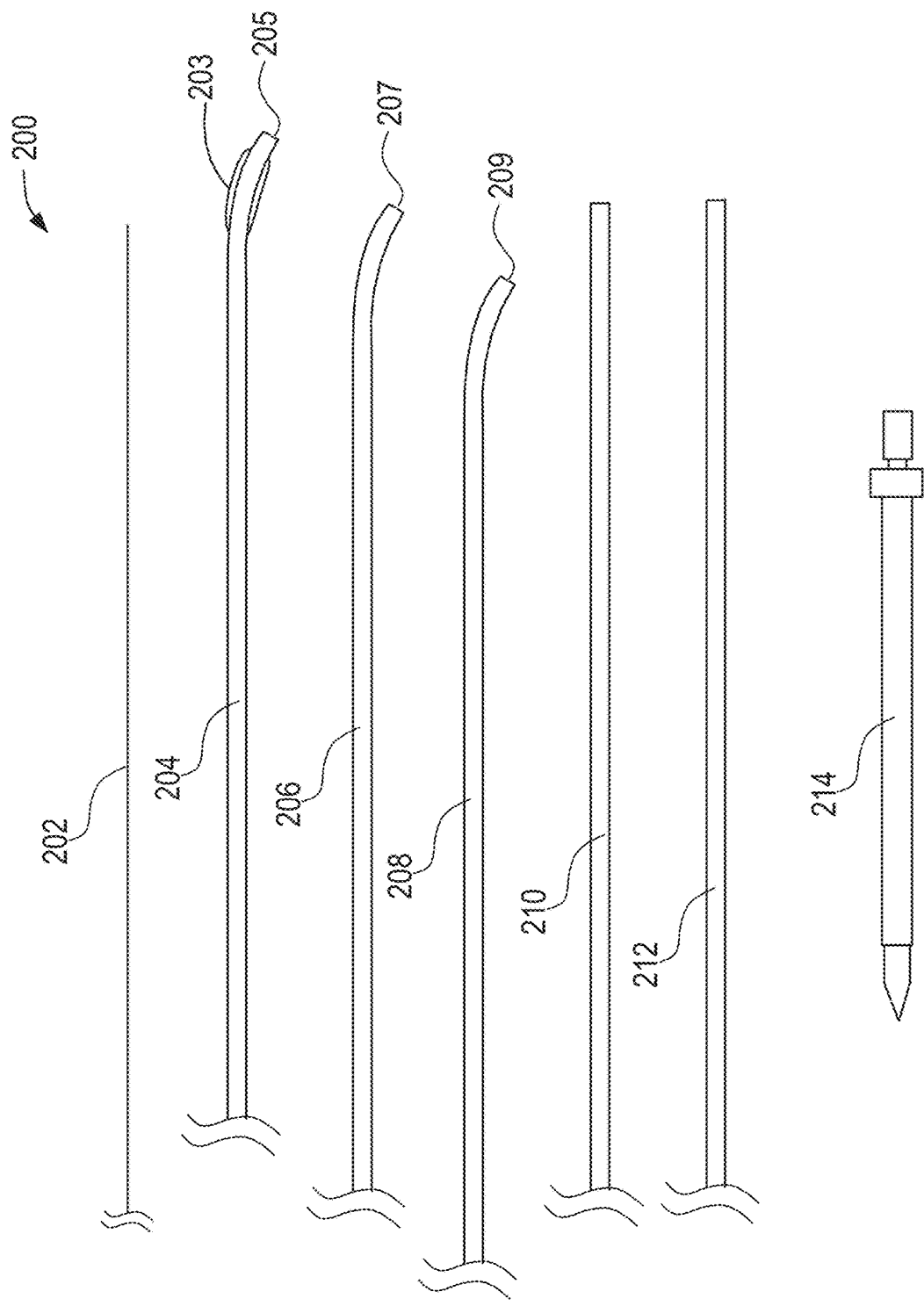
FIG. 2 is an exemplary kit for implanting the extravascular bypass system of FIG. 1.

Referring now to FIG. 2, exemplary kit 200 for implanting the extravascular bypass system is provided. Kit 200 includes guidewire 202, first sheath 204, second sheath 206, third sheath 208, upstream bypass stent delivery sheath 210, downstream bypass stent delivery sheath 212, and percutaneous tunneler system 214. Guidewire 202 has a length sufficient to span from a contralateral access point, e.g., within the patient's healthy leg, intravascularly across to the patient's sick leg, e.g., the leg having the occluded vessel to be bypassed, to a point downstream of the occlusion, e.g., below the patient's knee.

First sheath 204 is sized and shaped to be inserted into the patient via the contralateral access point such that distal end 205 of sheath 204 is positioned within the target occluded blood vessel upstream of the occlusion. Accordingly, sheath 204 has a length sufficient to span from the contralateral access point in the patient's healthy leg, across to the other leg, to the position upstream of the occluded vessel in the patient's sick leg. Sheath 204 is flexible and may easily be maneuvered through the patient's vasculature. For example, the distal region of sheath 204 may be biased toward a curled configuration. In addition, sheath 204 has a guidewire lumen sized and shaped to receive guidewire 202 therethrough.

In addition, as shown in FIG. 2, first sheath 204 further may include inflatable balloon 203 positioned along the distal region of sheath 204 adjacent to distal end 205. Balloon 203 may be in fluid communication with a source of inflation fluid external to the patient's body via a inflation lumen extending through sheath 204. Accordingly, balloon 203 may be inflated and deflated between a collapsed delivery state and an expanded occlusion state. For example, in the expanded occlusions state, balloon 203 may have a diameter essentially equal to the inner diameter of the blood vessel to thereby prevent blood flow through the vessel during the implant procedure described in further detail below.

Second sheath 206 is sized and shaped to be inserted into the patient via a first access point, e.g., in the patient's sick leg, at a location upstream of the occluded vessel such that distal end 207 may rendezvous with distal end 205 of sheath 204. Accordingly, sheath 206 has a length sufficient to span from the first access point in to the position upstream of the occluded vessel in the patient's sick leg where distal end 205 of sheath 204 is positioned. Sheath 206 is flexible and may easily be maneuvered through the patient's vasculature. For example, the distal region of sheath 206 may be biased toward a curled configuration. In addition, sheath 206 has a guidewire lumen sized and shaped to receive guidewire 202 therethrough. Moreover, sheath 206 may be a tear-away sheath that may be removed from the guidewire and the patient while the guidewire remains in place during the implant procedure described in further detail below.

Third sheath 208 is sized and shaped to be inserted into the patient via a second access point, e.g., in the patient's sick leg, at a location downstream of the occluded vessel. Sheath 208 is flexible and may easily be maneuvered through the patient's vasculature. For example, the distal region of sheath 208 may be biased toward a curled configuration. In addition, sheath 208 has a guidewire lumen sized and shaped to receive guidewire 202 therethrough. Moreover, sheath 208 may be a tear-away sheath that may be removed from the guidewire and the patient while the guidewire remains in place during the implant procedure described in further detail below.

Upstream bypass stent delivery sheath 210 has a lumen extending therethrough sized and shaped to receive upstream bypass stent 102 in a collapsed delivery state for delivery to the target implant site upstream of the occlusion within the patient's vessel. For example, sheath 210 may have a length sufficient to span from the second access point downstream of the occlusion to the upstream implant site upstream of the occlusion to delivery stent 102 at the upstream implant site.

Downstream bypass stent delivery sheath 212 has a lumen extending therethrough sized and shaped to receive downstream bypass stent 110 in a collapsed delivery state for delivery to the target implant site downstream of the occlusion within the patient's vessel. For example, sheath 212 may have a length sufficient to span from the contralateral access point in the patient's healthy leg, across the patient's leg to the downstream implant site downstream of the occluded vessel to delivery stent 110 at the downstream implant site. Accordingly, the lumen of first sheath 204 may be sized and shaped to permit sheath 212 to pass therethrough. Alternatively, sheath 212 may have a length sufficient to span from the second access point downstream of the occluded vessel to the downstream implant site to delivery stent 110 at the downstream implant site.

Figure 3A:
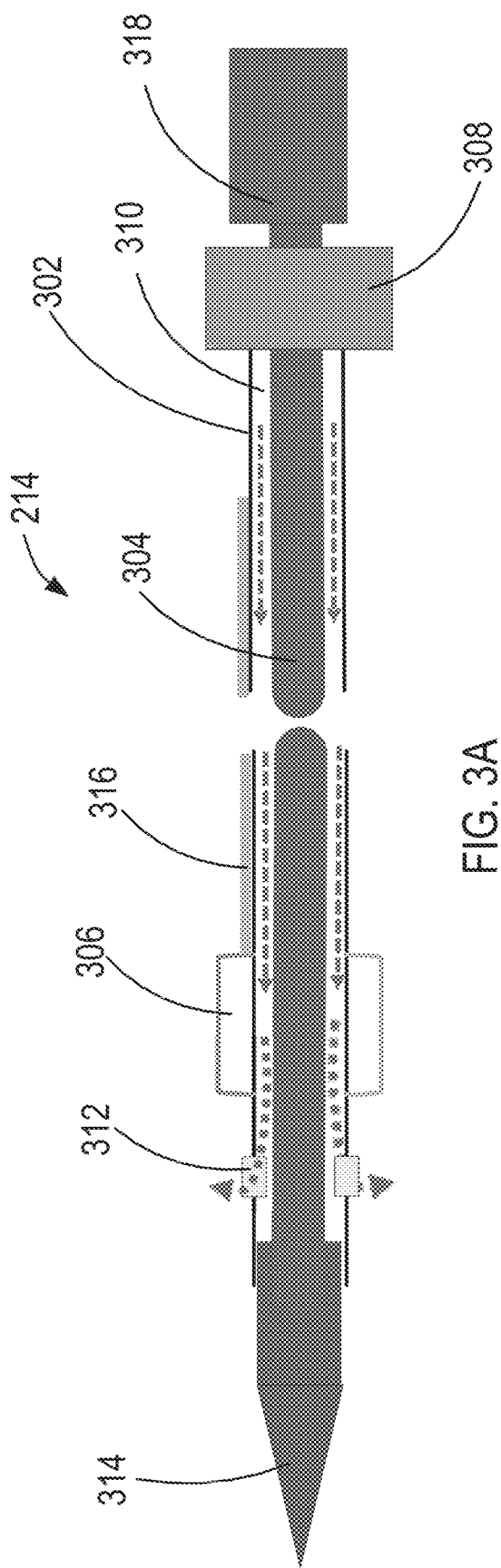
FIGS. 3A-3E illustrate the percutaneous tumescence tunneler of FIG. 2 constructed in accordance with the principles of the present invention.

Percutaneous tunneler system 214 may be, e.g., a percutaneous tumescence tunneler that may deliver tumescence local anesthesia to the tissue adjacent to at least the upstream implant site. For example, referring now to FIG. 3A, tunneler 214 includes tunneler 302, e.g., a shrink tube, and stiff trocar 304, having handle 308 coupled at the proximal region of trocar 304 for navigating system 214 through tissue, and tapered tip 314 coupled to the distal end of trocar 304 for dissecting through tissue during delivery of system 214. Tip 314 may have a length between 20 and 40 mm, and preferably 30 mm. In addition, trocar 304 may include adaptor 318 coupled it its proximal end, proximal to handle 308, for controller trocar 304.

Additionally, system 214 may include inflatable balloon 306 disposed on tunneler 302. Balloon 306 is in fluid communication with a source of inflation fluid via inflation tube 316. Accordingly, balloon 306 may be inflated and deflated between a collapsed delivery state and an expanded occlusion state. In the expanded state, balloon 306 functions to create a track in the fat lanes of the tissue to accommodate covered stent, as well as to prevent antegrade flow of local anesthesia during injection of the anesthesia as described in further detail below. For example, balloon 306 may have a diameter of between 5 and 15 mm, and preference 10 mm, and a length of between 30 and 50 mm, and preferably 40 mm.

Figure 3B:
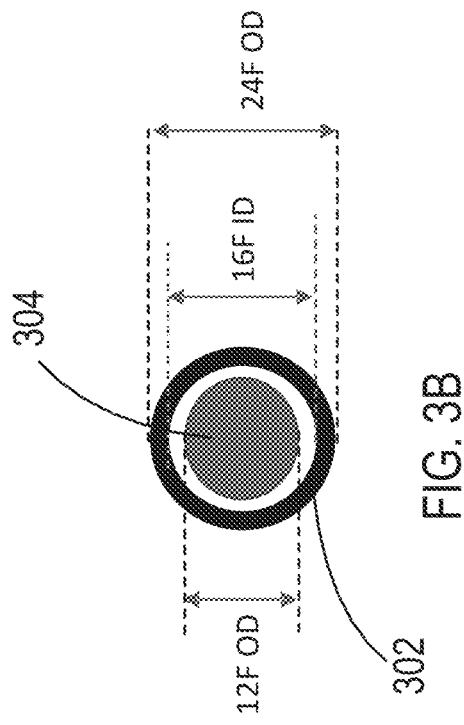

In addition, tunneler 302 may have one or more ports 312 disposed circumferentially around a distal region of tunneler 302. Ports 312 are in fluid communication with a source of tumescence local anesthesia via one or more lumens 310 positioned between tunneler 302 and trocar 304. As shown in FIG. 3B, trocar 304 may have an outer diameter of 12 F, and tunneler 302 may have an inner diameter of 16 F and an outer diameter of 24 F. Thus, tumescence local anesthesia may be injected in the tissue at the implant site adjacent to the distal region of system 214. For example, tumescence local anesthesia may be injected at a rate between 30 and 50 ml/min, and preferably 40 ml/min. As described above, balloon 306 may be inflated prior to injection of the tumescence local anesthesia to prevent antegrade flow, e.g., leakage, of the tumescence local anesthesia. Moreover, lumens 310 may be coupled to a 3-way tap at handle 308 to infusion of the tumescence local anesthesia.

Figure 3C:
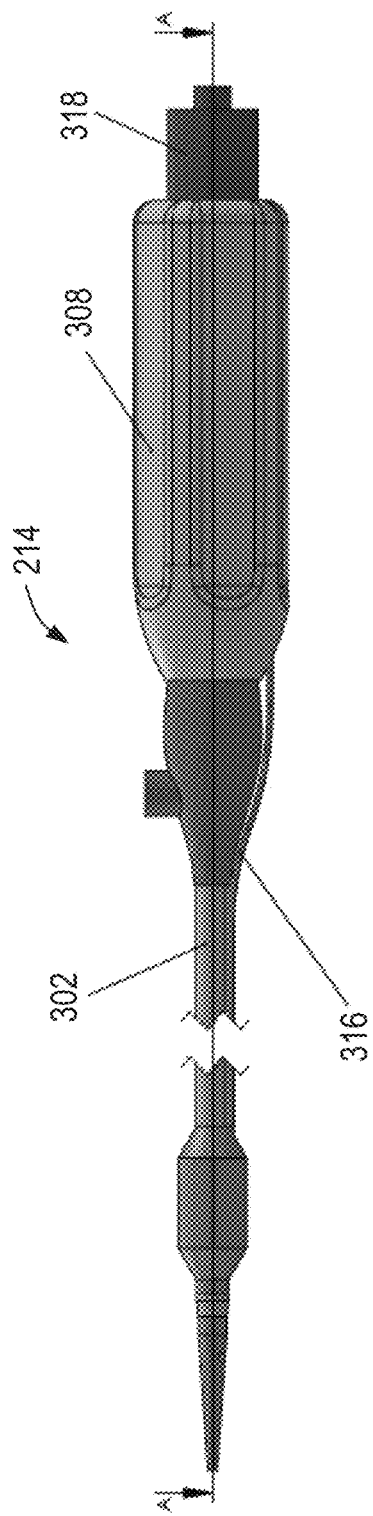
Figure 3D:
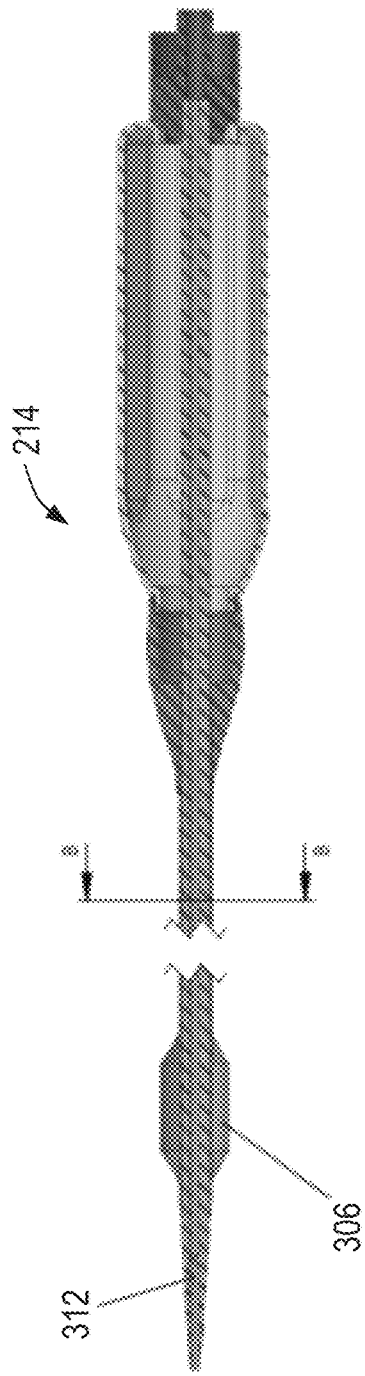
Figure 3E:
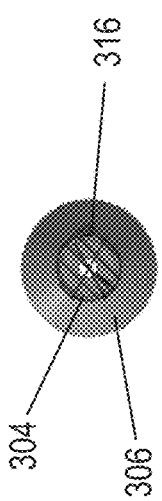

FIG. 3C illustrates an perspective view of system 214, and FIG. 3D illustrates a cross-section of system 214 along lines A-A of FIG. 3C. As shown in FIGS. 3C and 3D, handle 308 may include grooves for allowing the physician to comfortably and rigidly control system 214. Moreover, FIG. 3E illustrates a cross-section of system 214 along lines B-B of FIG. 3D. Although not shown, system 214 may be slightly curved for ease of access and control within the patient's body.

Figure 4:
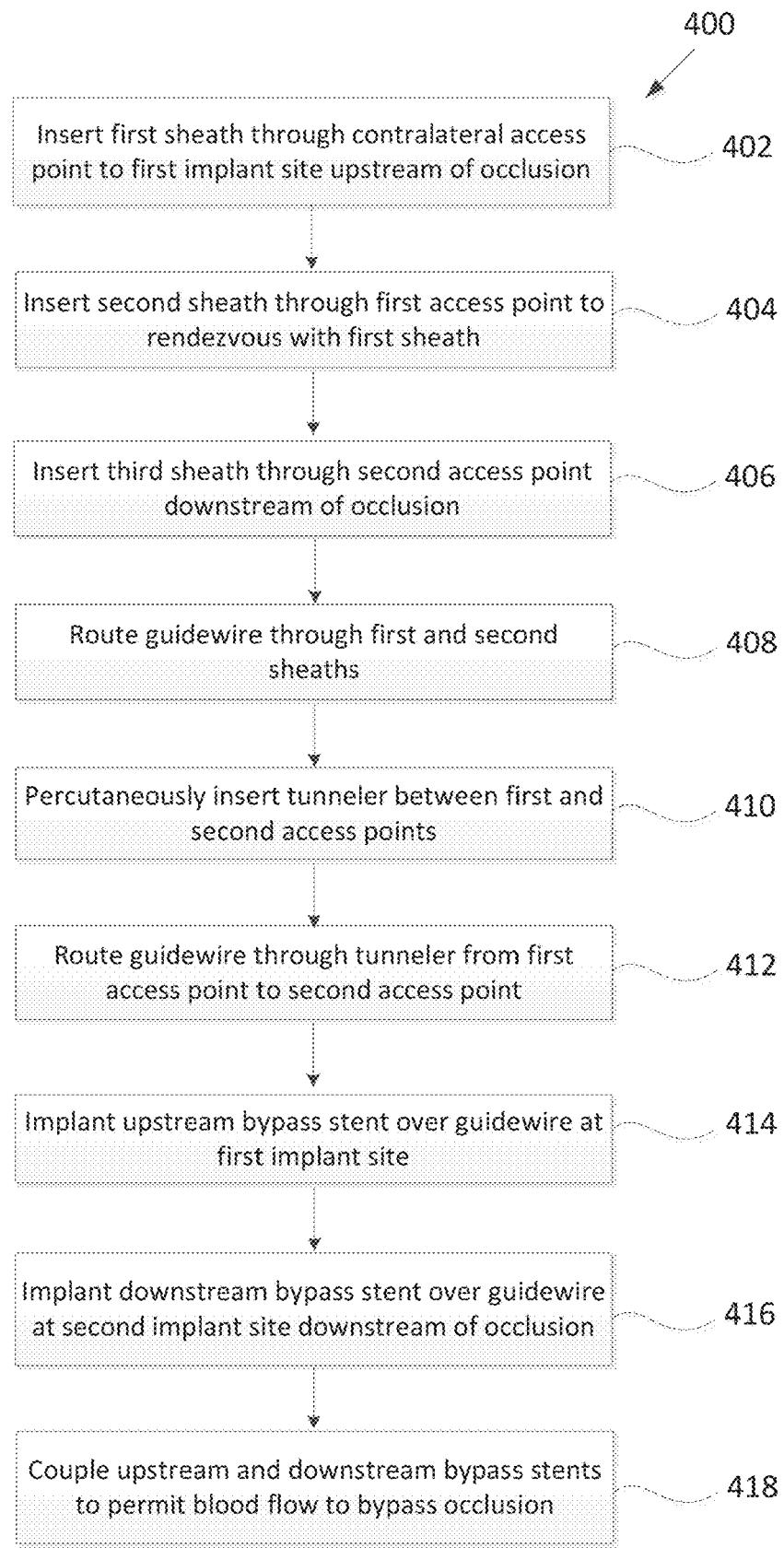
FIG. 4 is a flow chart of exemplary method steps for using the kit of FIG. 2 to implant the extravascular bypass system of FIG. 1 in accordance with the principles of the present invention.
Figure 5G:
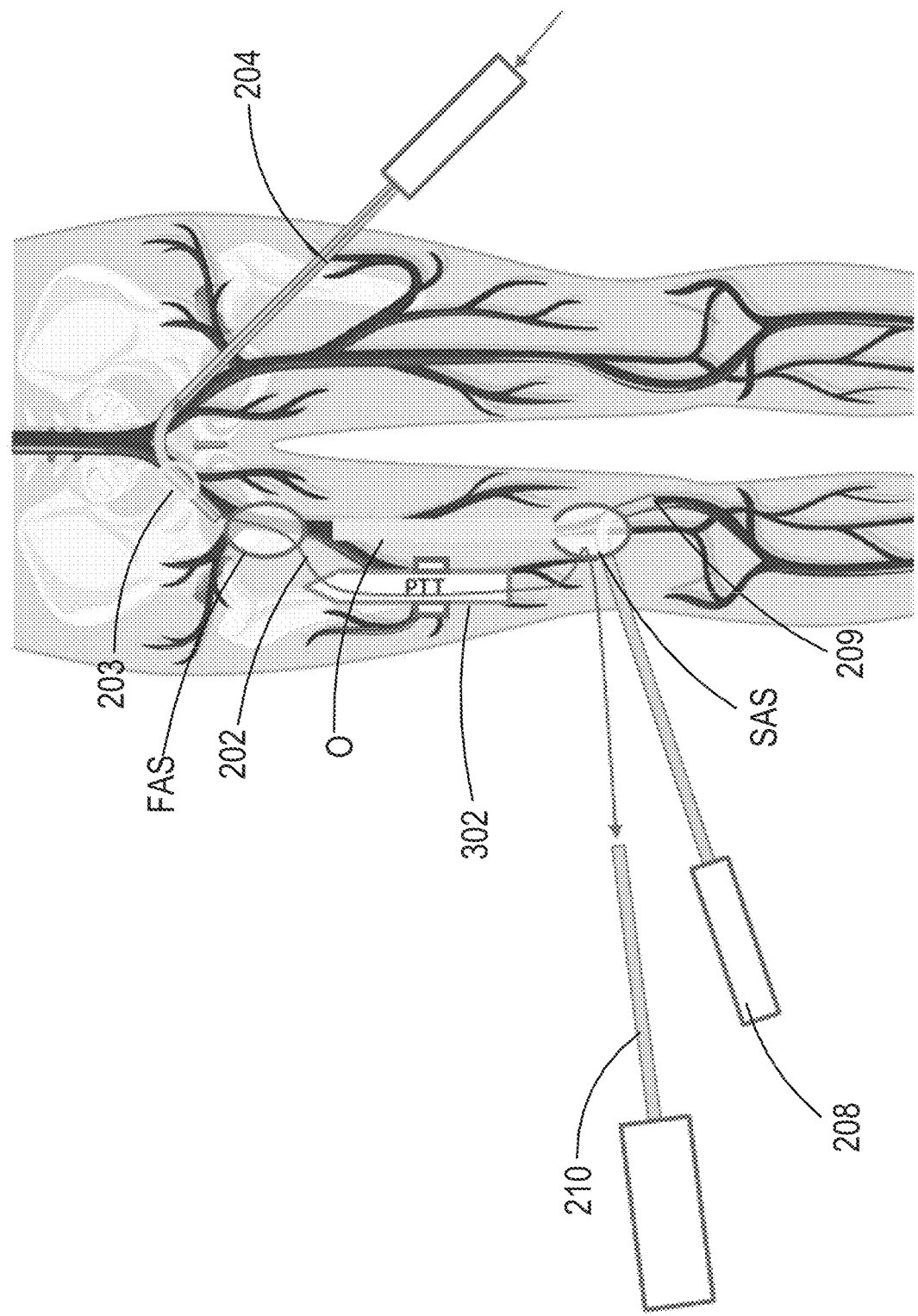

Referring now to FIG. 4, exemplary method 400 for using kit 200 to implant extravascular bypass system 100 is provided. Some of the steps of method 400 may be further elaborated by referring to FIGS. 5A-5L. At step 402, first sheath 204 is inserted within the patient through an incision at a contralateral access site, e.g., in the patient's healthy leg, and crossed over to the patient's sick leg. As illustrated in FIG. 5A, distal end 205 of sheath 204 is positioned across the patient to the patient's sick leg, at a location upstream of occlusion 0, adjacent to first access site FAS. Guidewire 202 may be inserted through the lumen of sheath 204.

At step 404, second sheath 206 is inserted within the patient through an incision at first access site FAS until distal end 207 is brought into contact with distal end 205 of sheath 204 at rendezvous point RP as shown in FIG. 5B. Moreover, guidewire 202 may be moved from within sheath 204 to within the lumen of sheath 206, e.g., using a snare device. In addition, as illustrated in FIG. 5B, an incision may be made at second access site SAS at a point downstream of occlusion O. At step 406, third sheath 208 is inserted within the patient through the incision at second access site SAS in an antegrade direction, e.g., within the patient's popliteal artery, as shown in FIG. 5C.

At step 408, guidewire 202 is routed through sheath 204 and sheath 206, if not already done so prior. At step 410, percutaneous tunneler system 214 is percutaneously inserted within the patient through the incision at second access point SAS toward first access site FAS such that system 214 extends percutaneously between first access site FAS and second access site SAS as shown in FIG. 5D. Next, balloon 306 of system 214 may be inflated and tumescence local anesthesia may be injected into the tissue. Trocar 304 may then be removed, leaving tunneler 302 in place extending between first access site FAS and second access site SAS.

At step 412, guidewire 202 is routed from second sheath 206 through the lumen of tunneler 302 from the direction of first access site FAS toward second access site SAS, and out of the patient's body as shown in FIG. 5D. As illustrated in FIG. 5E, balloon 203 of sheath 204 may be inflated to occlude the target vessel, thereby preventing blood flow through the vessel. For example, FIG. 5F illustrates balloon 203 of sheath 204 in the expanded occlusion state within the vessel.

Next, at step 414, upstream bypass stent delivery sheath 210 is used to deliver and implant upstream bypass stent 102 at the implant site upstream of the occluded vessel. As shown in FIG. 5E, sheath 210 is advanced over guidewire 202 and through tunneler 302 to the upstream implant site adjacent to first access site FAS. Peel-away sheath 206 may be removed from guidewire 202 and the patient at this time, and thus guidewire 202 extends from within sheath 204 and tunneler 302 as shown in FIG. 5G.

As shown in FIG. 5H, sheath 210 may then be retracted to expose stent 102 such that stent 102 transitions from the collapsed delivery state to the expanded deployed state at the upstream implant site. Accordingly, inlet 104 of stent 102 will be positioned within the target blood vessel, outlet 108 will be positioned within the same vessel downstream of inlet 104, but upstream of occlusion 0, and outlet 106 will extend extravascularly out of the vessel into extravascular tissue. Tunneler 302 may now be removed.

In addition, balloon 203 of sheath 204 may be deflated, and sheath 204 may be moved distally in the direction of first access site FAS, and re-inflated to prevent bleeding through the bypass of the vessel as shown in FIG. 5I. In addition, as shown in FIG. 5I, guidewire 202 may then be routed into the lumen of third sheath 208 through the incision at second access site SAS, e.g., below the patient's knee. Stent 208 may then be removed from guidewire 202 and the patient while guidewire 202 remains in place.

Figure 5J:
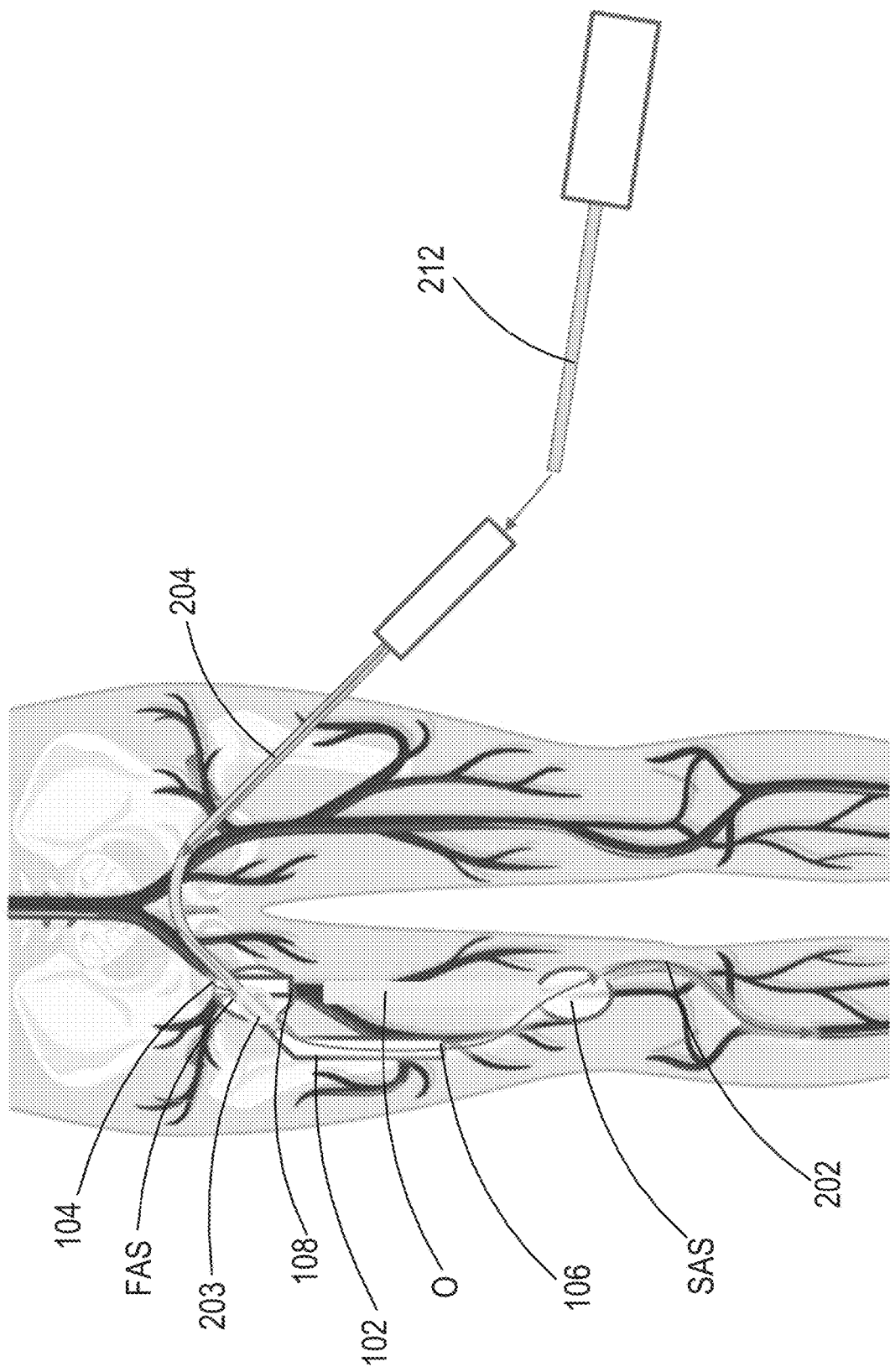

At step 416, downstream bypass stent delivery sheath 212 is used to deliver and implant downstream bypass stent 110 at the implant site downstream of the occluded vessel. For example, as shown in FIG. 5J, sheath 212 may be inserted over guidewire 202, through the lumen of sheath 204 at the proximal end of sheath 204, and moved through the contralateral access point, across the patient to the sick leg, until the distal end of sheath 212 is positioned adjacent second access site SAS adjacent to the downstream implant site downstream of the occluded vessel. Sheath 212 may then be retracted to expose stent 110 such that stent 110 transitions from the collapsed delivery state to the expanded deployed state at the downstream implant site. Accordingly, inlet 114 of stent 110 will be positioned within the target blood vessel downstream of occlusion O, outlet 116 will be positioned within the same vessel downstream of inlet 114, and inlet 112 will extend extravascularly out of the vessel into extravascular tissue.

Figure 5K:
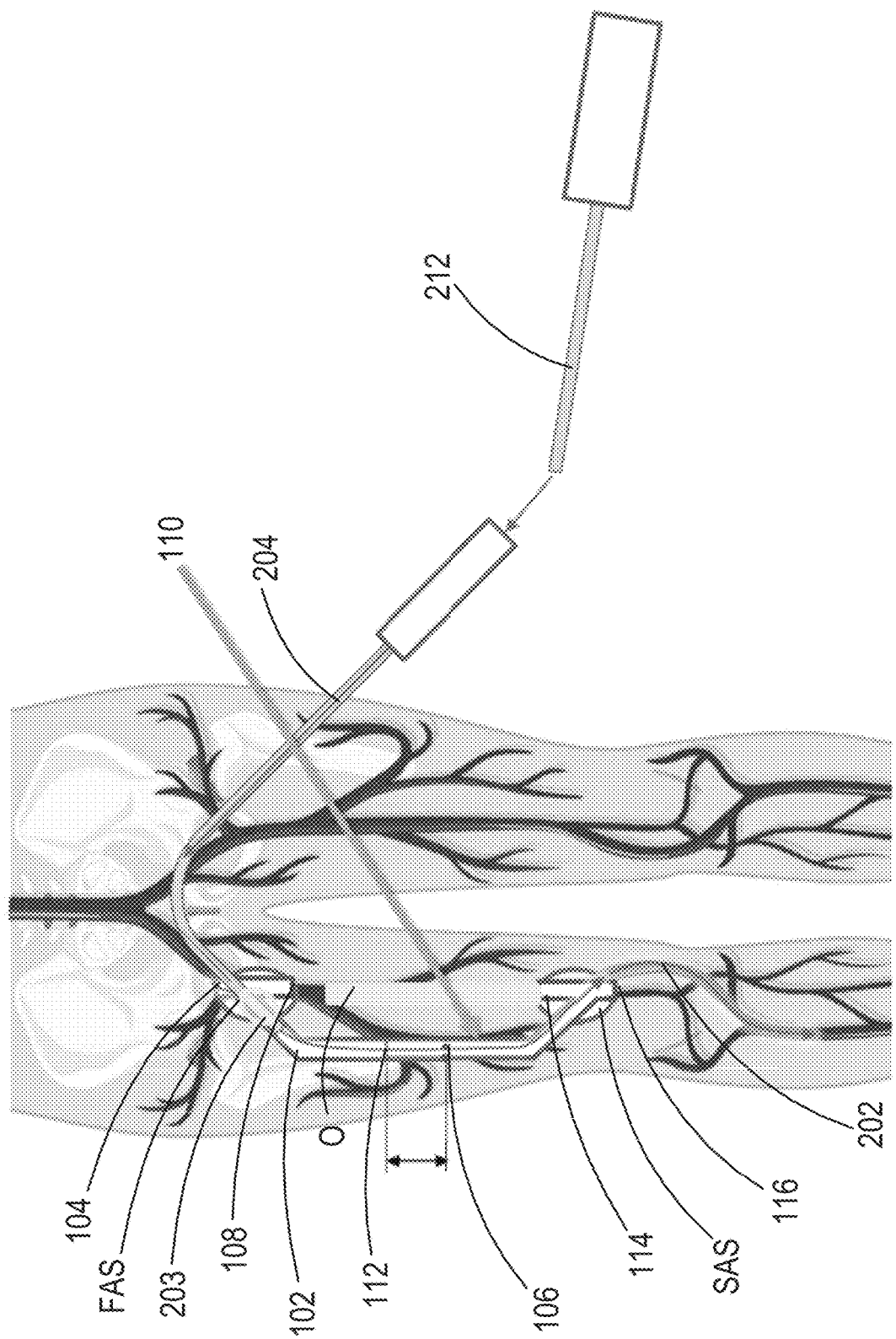
Figure 5L:
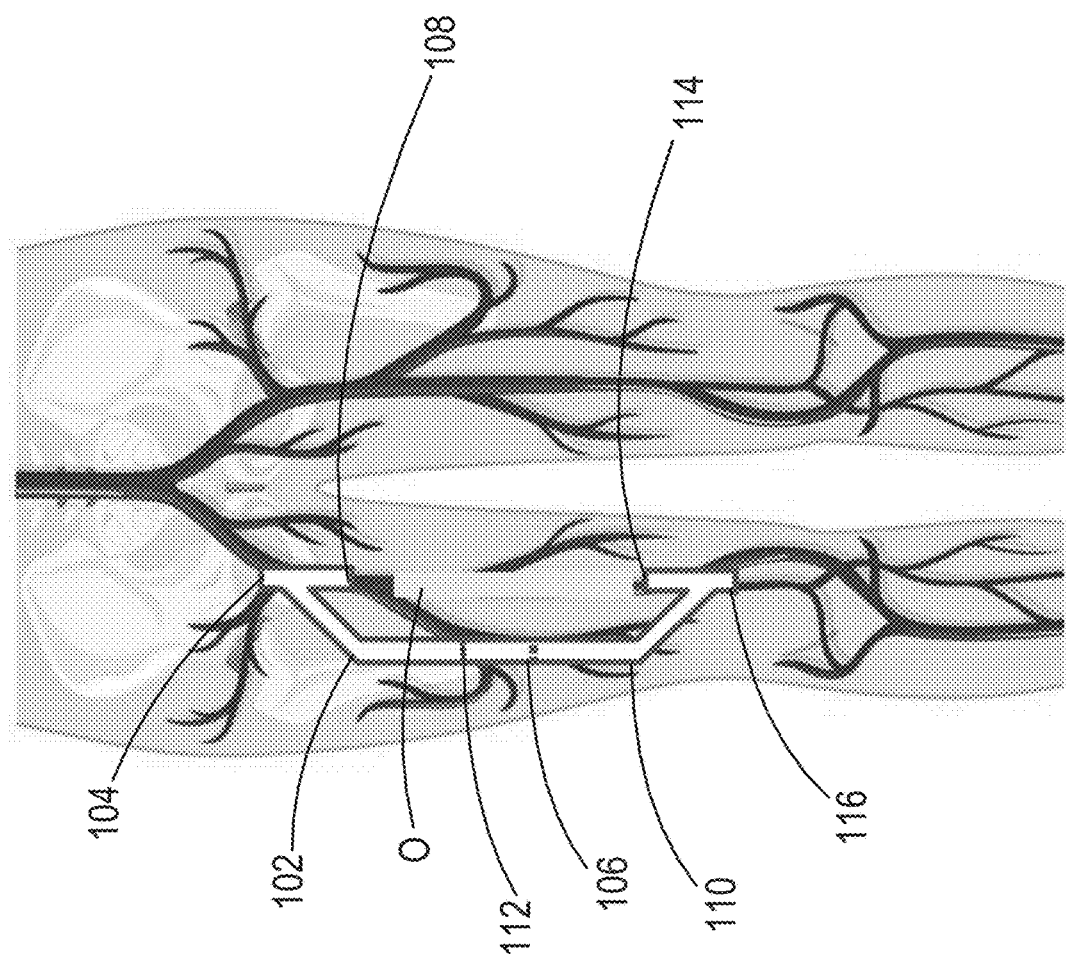

At step 418, outlet 106 of stent 102 is coupled to inlet 112 of stent 110 as shown in FIG. 5K, thereby permitting blood to enter inlet 104, and bypass occlusion O via outlet 106, inlet 112, and outlet 116, as well as continue to flow through occlusion O via outlet 108, inlet 114, and outlet 116. As shown in FIG. 5K, stent 102 and stent 110 may overlap a predetermined distance. Finally, balloon 203 of sheath 204 may be deflated, and all the remaining sheaths and guidewire 202 may be removed from the patient, and all the incisions may be closed, as shown in FIG. 5L.

Referring now to FIGS. 6A to 6C, alternative exemplary extravascular bypass stent 600 is described. Stent 600 is constructed similarly to stent 102 of FIG. 1. For example, inlet 602 is similar to inlet 104 and outlet 604 is similar to outlet 106. However, stent 600 differs from stent 102 such that instead of outlet 108 disposed at the end of a tube, outlet 606 includes one or more fenestrations disposed directly on stent 600, as shown in FIG. 6B. As illustrated in FIG. 6C, when stent 600 is positioned within the target vessel at the upstream implant site, outlet 604 extends out of the vessel extravascularly, and outlet 606 is positioned to permit at least a portion of the blood flow entering inlet 602 to exit through fenestrations 606 and through the occluded vessel toward occlusion O. As will be understood by a person having ordinary skill in the art, the downstream bypass stent may be similarly constructed in accordance with the principles of the present invention.

Referring now to FIGS. 7A to 7D, another exemplary extravascular bypass stent 700 is described. Stent 700 is constructed similarly to stent 600 of FIGS. 6A-6C. For example, inlet 702 is similar to inlet 602 and outlet 704 is similar to outlet 606. However, stent 700 differs from stent 600 such that instead of one or more fenestrations 606, stent 700 includes outlet 706. Outlet 706 may be formed by creating a circumferential along a portion of a cylindrical tube, wherein the proximal end of the cylindrical tube has inlet 702. The portion of the cylindrical tube distal to the cut may be pushed radially inward to creating an opening to accommodate a smaller diameter curved tube, wherein the distal end of the curved tube has outlet 704. Accordingly, when the curved tube is positioned within the opening of the larger cylindrical tube, outlet 703 is positioned adjacent outlet 702. Accordingly, as shown in FIG. 7D, when stent 700 is positioned within the target vessel at the upstream implant site, outlet 704 extends out of the vessel extravascularly, and outlet 706 is positioned to permit at least a portion of the blood flow entering inlet 702 to exit through outlet 706 and through the occluded vessel toward occlusion O. The blood that enters inlet 702 and does not exit via outlet 706 will be redirected through inlet 703 and outlet 704. As will be understood by a person having ordinary skill in the art, the downstream bypass stent may be similarly constructed in accordance with the principles of the present invention.

Referring now to FIGS. 8A and 8B, another alternative exemplary extravascular bypass stent 800 is described. Stent 800 is constructed similarly to stent 102 of FIG. 1. For example, inlet 802 is similar to inlet 104 and outlet 804 is similar to outlet 106. However, stent 800 differs from stent 102 such that instead of outlet 108 disposed at the end of a tube that is positioned within the same vessel as inlet 102, outlet 806 is disposed at the end of a tube that bends away from the longitudinal axis of the tube having inlet 802. Thus, as illustrated in FIG. 8B, when stent 800 is positioned within the target vessel at the upstream implant site, outlet 804 extends out of the vessel extravascularly, and outlet 806 extends into another vessel branch, e.g., the profunda femoris artery. As will be understood by a person having ordinary skill in the art, the downstream bypass stent may be similarly constructed in accordance with the principles of the present invention.

Figure 9:
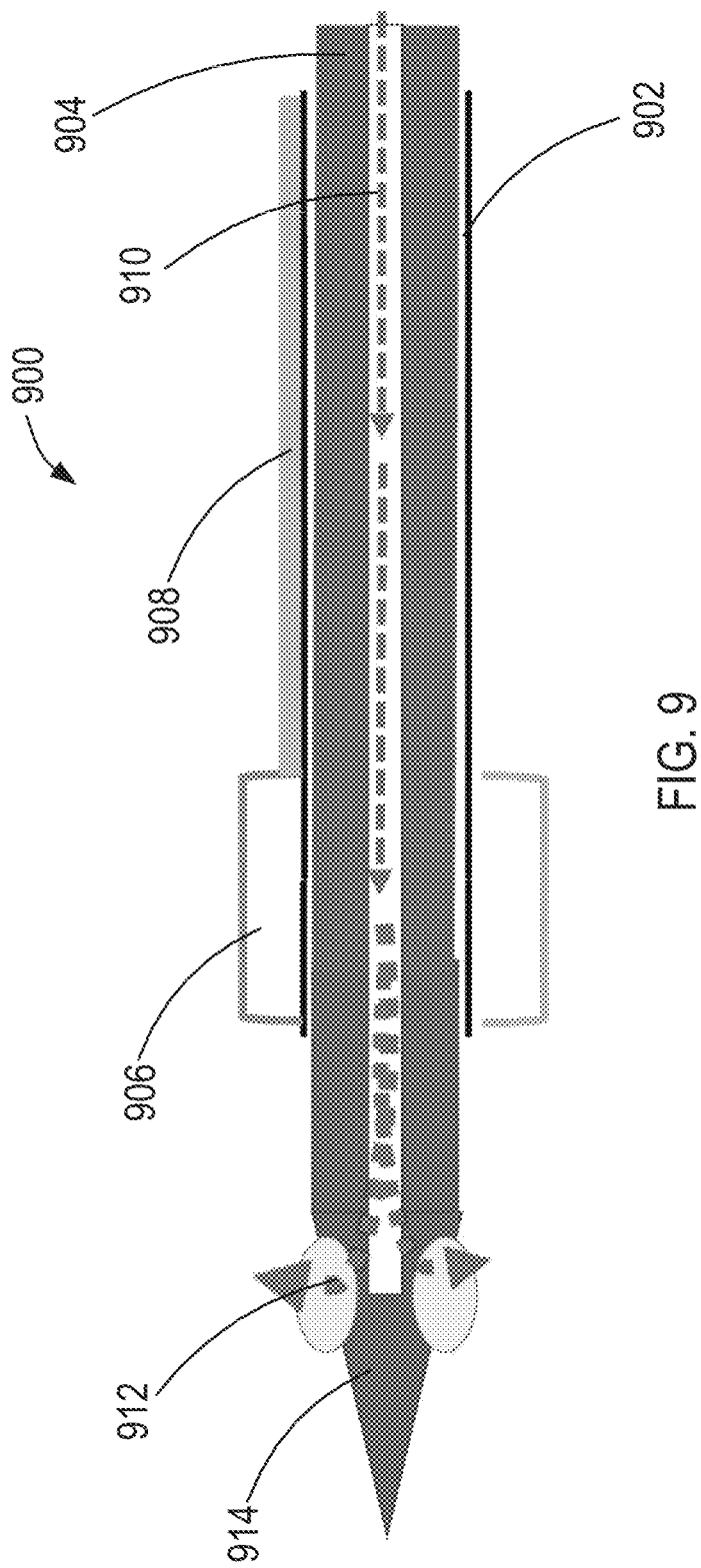
FIG. 9 illustrates an alternative percutaneous tumescence tunneler constructed in accordance with the principles of the present invention.

Referring now to FIG. 9, alternative exemplary percutaneous tunneler system 900 is provided. System 900 is constructed similar to system 214 of FIG. 3A. For example, tunneler 902 is similar to tunneler 302, balloon 906 coupled to inflation tube 908 is similar to balloon 306 coupled to inflation tube 316, and tapered tip 914 is similar to tapered tip 314. System 900 differs from system 214 such that instead of one or more lumens 310 in fluid communication with ports 312, trocar 902 has lumen 910 extending therethrough to fluidicly couple one or more ports 912 to a source of tumescence local anesthesia. In addition, ports 912 are disposed circumferentially along the surface of tip 914.

While various illustrative embodiments of the invention are described above, it will be apparent to one skilled in the art that various changes and modifications may be made herein without departing from the invention. The appended claims are intended to cover all such changes and modifications that fall within the true spirit and scope of the invention.

What is claimed:

1. An extravascular bypass kit comprising:
   an upstream bypass stent comprising:
      an upstream bypass inlet configured to be implanted within at least one blood vessel at a first implant site upstream of an occlusion within the at least one blood vessel;
      a first upstream bypass outlet in fluid communication with the upstream bypass inlet and configured to be implanted extravascularly; and
      a second upstream bypass outlet in fluid communication with the upstream bypass inlet, the second upstream bypass outlet configured to direct blood flow from the upstream bypass inlet toward the second upstream bypass outlet;
   a downstream bypass stent comprising:
      a first downstream bypass inlet configured to be implanted extravascularly and to be coupled to the first upstream bypass outlet of the upstream bypass stent such that the first downstream bypass inlet is in fluid communication with the upstream bypass inlet of the upstream bypass stent; and
      a downstream bypass outlet configured to be implanted within the at least one blood vessel at a second implant site downstream of the occlusion within the at least one blood vessel, the downstream bypass outlet in fluid communication with the upstream bypass inlet of the upstream bypass stent via the first upstream bypass outlet of the upstream bypass stent and the first downstream bypass inlet such that blood flow through the upstream bypass inlet is directed to bypass the occlusion via the first upstream bypass outlet, the first downstream bypass inlet, and the downstream bypass outlet;
   a first sheath having a distal end configured to be positioned within the vessel adjacent the first implant site via a contralateral access point, the first sheath having a length extending at least from the contralateral access point to the first implant site;
   a second sheath having a distal end configured to be positioned adjacent the distal end of the first sheath via a first access point upstream of the occlusion within the vessel, the second sheath having a length extending at least from the first access point to the distal end of the second sheath;
   a percutaneous tumescence tunneler having a length extending from the first access point to a second access point downstream of the occlusion within the vessel; and
   a first delivery sheath having a lumen extending therethrough sized and shaped to deliver the upstream bypass stent in a collapsed delivery state to the first implant site.

2. The kit of claim 1, wherein the downstream bypass stent further comprises a second downstream bypass inlet in fluid communication with the downstream bypass outlet, the second downstream bypass inlet positioned downstream of the occlusion within the at least one blood vessel such that blood flow through the upstream bypass inlet is directed out the downstream bypass outlet via the second upstream bypass outlet and the second downstream bypass inlet.

3. The kit of claim 2, wherein the downstream bypass stent further comprises a tube having a first end and a second end, the first end coupled to the second downstream bypass inlet, and the second end configured to be implanted within the vessel at a location downstream of the occlusion within the vessel, the second end having a tube inlet in fluid communication with the second downstream bypass inlet of the downstream bypass stent.

4. The kit of claim 1, wherein the first upstream bypass outlet of the upstream bypass stent and the first downstream bypass inlet of the downstream bypass stent are configured to be implanted subcutaneously.

5. The kit of claim 1, wherein the second upstream bypass outlet of the upstream bypass stent comprises one or more fenestrations.

6. The kit of claim 1, wherein the upstream bypass stent further comprises a tube having a first end and a second end, the first end coupled to the second upstream bypass outlet, and the second end configured to be implanted within the vessel at a location upstream of the occlusion within the vessel, the second end having a tube outlet in fluid communication with the second upstream bypass outlet of the upstream bypass stent.

7. The kit of claim 1, wherein the distal end of the first sheath comprises an inflatable balloon configured to transition between a deflated delivery state and an inflated state having a size and shape configured to stop blood flow through the vessel.

8. The kit of claim 1, further comprising a third sheath having a distal end configured to be positioned within the vessel adjacent the second implant site via the second access point downstream of the occlusion within the vessel, the third sheath having a length extending at least from the second access point to the distal end of the third sheath.

9. The kit of claim 8, wherein at least one of the second or third sheath is a peel-away-sheath.

10. The kit of claim 8, further comprising a second delivery sheath, the second delivery sheath having a lumen extending therethrough sized and shaped to deliver the downstream bypass stent in a collapsed delivery state to the second implant site such that the first upstream bypass outlet of the upstream bypass stent and the first downstream bypass inlet of the downstream bypass stent overlap in a deployed state.

11. The kit of claim 10, further comprising a guidewire having a length extending at least from the contralateral access point to the first access point and the second access point.

12. A method for extravascularly bypassing an occlusion within a vessel of a patient, the method comprising:

introducing a distal end of a first sheath through a contralateral access point to a position adjacent a first implant site upstream of the occlusion within the vessel;

introducing a distal end of a second sheath through a first access point upstream of the occlusion to rendezvous with the distal end of the first sheath;

routing a guidewire through the first sheath and the second sheath;

percutaneously inserting a tunneler between the first access point and a second access point downstream of the occlusion;

routing the guidewire through the tunneler from the first access point to the second access point;

introducing a first delivery sheath over the guidewire from the second access point to the first access point, the first delivery sheath having an upstream bypass stent disposed therein in a collapsed delivery state, the upstream bypass stent having an upstream bypass inlet, a first upstream bypass outlet extending extravascularly from the first implant site, the first upstream bypass outlet in fluid communication with the upstream bypass inlet, and a second upstream bypass outlet upstream of the occlusion in fluid communication with the upstream bypass inlet;

implanting the upstream bypass stent at the first implant site using the first delivery sheath;

implanting a downstream bypass stent at a second implant site downstream of the occlusion within the vessel, the downstream bypass stent having a first downstream bypass inlet extending extravascularly from the second implant site, and a downstream bypass outlet in fluid communication with first and second downstream bypass inlets;

coupling the first upstream bypass outlet of the upstream bypass stent with the first downstream bypass inlet of the downstream bypass stent; and permitting blood to flow through the upstream bypass inlet to bypass the occlusion via the first upstream bypass outlet, the first downstream bypass inlet, and the downstream bypass outlet, and to flow through the upstream bypass inlet to the downstream bypass outlet via the second upstream bypass outlet.

13. The method of claim 12, wherein the downstream bypass stent further comprises a second downstream bypass inlet in fluid communication with the downstream bypass outlet downstream of the occlusion, thereby permitting blood to flow through the upstream bypass inlet to the downstream bypass outlet via the second upstream bypass outlet and the second downstream bypass inlet.

14. The method of claim 12, wherein implanting the upstream bypass stent at the first implant site comprises
introducing a distal end of a third sheath through the second access point downstream of the occlusion.

15. The method of claim 12, further comprising inflating an inflatable balloon disposed at the distal end of the first sheath to stop blood flow through the vessel.

16. The method of claim 14, further comprising:
routing the guidewire through the third sheath at the second access point; and
removing the third sheath from the patient.

17. The method of claim 12, wherein implanting the downstream bypass stent at the second implant site comprises:
introducing a second delivery sheath over the guidewire from the contralateral access point to the second implant site, the second delivery sheath having the downstream bypass stent disposed therein in a collapsed delivery state; and
implanting the downstream bypass stent at the second implant site using the second delivery sheath.

* * * * *